United States Patent
Asar

(10) Patent No.: US 6,477,266 B1
(45) Date of Patent: Nov. 5, 2002

(54) VISION COMPARISON INSPECTION SYSTEM GRAPHICAL USER INTERFACE

(75) Inventor: Madhu Purushotum Asar, Reynoldsburg, OH (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/210,068

(22) Filed: Dec. 11, 1998

(51) Int. Cl.[7] .................................................. G06K 9/00
(52) U.S. Cl. ...................................... 382/147; 382/144
(58) Field of Search ........................... 716/1, 4, 11, 19; 250/492.2, 492.1; 382/141, 144, 145, 147, 151, 149, 142, 143, 146; 700/121, 124, 125

(56) References Cited

U.S. PATENT DOCUMENTS

| | | | | |
|---|---|---|---|---|
| 4,496,971 A | * | 1/1985 | West et al. .................. | 358/106 |
| 5,157,762 A | * | 10/1992 | Snietka ........................ | 395/129 |
| 5,663,569 A | * | 9/1997 | Hayano ................. | 250/559.49 |
| 5,697,699 A | * | 12/1997 | Seo et al. .................... | 362/252 |

OTHER PUBLICATIONS

Electronic Packaging Co., "Presenting The New 5400 High Precision, Loaded Board A.A.O.I. Station.".
Electronic Packaging Co., "Animated Automatic Optical Inspection Station Operators Manual.".

* cited by examiner

Primary Examiner—Andrew W. Johns
Assistant Examiner—Seyed Azarian
(74) Attorney, Agent, or Firm—Walter W. Duft

(57) ABSTRACT

A vision comparison inspection system is disclosed for use in a printed circuit assembly production line having a plurality of component processing locations and a conveyor system for transporting circuit assemblies between processing locations in an upstream to downstream work flow direction. The vision comparison inspection system includes a printed circuit assembly image capture and inspection conveyor disposed in the production line, the image capture and inspection conveyor being adapted to receive printed circuit assemblies from an upstream portion of the production line and to transport the printed circuit assemblies to a downstream portion of the production line for subsequent processing. An electronic imaging device is fixedly positioned to capture an image of a printed circuit assembly located on the image capture and inspection conveyor. A lighting system is mounted for illuminating a printed circuit assembly located in the field of view of the imaging device. A position control system positions a printed circuit assembly within the field of view of the imaging device. An imaging control system including a programmed image processing computer, an input device, and an electronic display device presenting a graphical user interface are provided for alternatingly displaying on the display device a stored image of a known good printed circuit assembly and an image of a printed circuit assembly under test, whereby defects in the printed circuit assembly under test can be visually identified.

44 Claims, 18 Drawing Sheets

VISION COMPARISON INSPECTION SYSTEM GRAPHICAL USER INTERFACE

CROSS-REFERENCE TO RELATED APPLICATIONS

This application relates to two applications filed on even data herewith by the same inventor, namely, application Ser. No. 09/210,070, entitled "Vision Comparison Inspection System" and application Ser. No. 09/209,709, entitled, "Vision Comparison Inspection System Camera and Lighting Arrangement."

BACKGROUND OF THE INVENTION

1. Field of the Invention

This invention relates to the production of printed circuit assemblies, and more particularly, to the vision inspection of mounted printed circuit components for defect identification and resolution.

2. Description of the Prior Art

A printed circuit assembly may have a large number and variety of components mounted on one or both sides of a printed circuit board. After component installation, but before final soldering, it is desirable to inspect each component-bearing side of the board for correct component assembly. This entails a check for wrong components, reversed components, broken components, mis-wired components or wire jumpers, and other defects.

Component-side inspection of circuit boards is often performed manually, either with or without the aid of optical magnification. Manual inspection is based on the inspector's familiarity with the product or by comparing the printed circuit assembly against a known reference such as a document, photograph, or an actual known good assembly. Such comparisons tend to be tedious and error prone because the inspector must repeatedly alternate attention between the reference and the board being tested ("Test Board"). As a result, manual component-side inspection of circuit boards is usually performed on a sample basis or is performed as a first board check before running many new boards.

As an alternative to manual inspection, automatic vision systems using roving cameras or line scan imagers have been utilized in some printed circuit assembly inspection applications. In an automatic system, many similar printed circuit assemblies are presented to the system such that it can learn the acceptance and rejection criteria. Optical character and shape recognition may also be used in conjunction with board data such as CAD generated information. Such systems can be very complex and prohibitively expensive. They are most effective in low product mix/high product volume environments.

A third approach to printed circuit assembly inspection, representing a compromise between manual and automatic inspection systems, is Blink Overlay Comparison. According to this method, alternating images of a known good board ("Golden Board") and a Test Board are repeatedly presented to a human operator. The two images appear in alternating fashion at the same visual position in the field of view of the observer. If the two boards are exactly alike and their images are presented to an observer in alternating fashion at some rate (such as five times per second), then the observer will not notice any movement of the images. On the other hand, if there are any differences between the two boards, then only the parts of the images with the differences will flash at the animation rate. These differences are generally due to the assembly defects mentioned above. By displaying the two images in the same visual position, the movement of the observer's attention and focus is eliminated. This increases the speed and accuracy of the inspection.

Several approaches to Blink Overlay Comparison have been used in the past. One such implementation is based on a pure optical comparison. In this method, two optical imaging systems are used in conjunction with a shutter system. The Golden Board is fixtured in a frame at a precision location under the lens of one of the imaging systems. The Test Board is similarly fixtured under the lens of the other imaging system. The two fixtures that hold the boards are coupled mechanically so that they can be moved simultaneously in X-Y directions under their respective lenses. The images from the two lenses are alternately displayed through a common optical eyepiece as in a microscope. Alternation between the two images is achieved with a motorized shutter system. Because the two boards are fixtured using a common reference, such as their respective tooling holes, their images are presented in the same relative position in the eye piece as they appear during alternate intervals.

In another implementation of Blink Overlay Comparison, the optical imaging systems described above are replaced with standard broadcast-grade color video cameras. The optical viewing system is replaced with a color monitor. The fixturing for the Golden Board and the Test Board is similar to that used in the optical system. The images of the two boards are electronically switched and alternatingly displayed on the video monitor.

Both of the foregoing Blink Overlay Comparison systems suffer from several basic problems. First, these systems require that the Golden Board be physically present. This means that an inventory of Golden Boards needs to be maintained. As an example, if a facility produces 100 different types of boards at an average cost of $500.00, then a $50,000 inventory of Golden boards is tied up at all times. Second, both the Golden Board and the Test Board must be placed very accurately in their respective fixtures so that the two images line up properly. Third, due to the limited resolution of the optical and video systems, only a very small portion of the Golden Board and the Test Board can be viewed at one time. This requires many movements of the two boards under the lenses.

One prior art system overcomes certain of these problems. It includes a downward looking video camera that is mounted on an X-Y positionable mounting assembly and a precision board-holding fixture. First, a Golden Board is placed on the precision board holder using the Golden Board's tooling holes. This provides a repeatable position for the Golden Board and the subsequently imaged Test Board. The video camera has a limited resolution, for example, 500×500 pixels. In order to read the value of components on a board for comparison purposes, the camera has to be zoomed in so close that on a typical 16"×16" board, only a very small portion (such as 4"×4") of the board is captured at one time. In that case, the camera moves and grabs images at 16 different locations on the Golden Board. In this way a library of images for each Golden Board is created and stored.

When running the production of any one board type, the Golden Board file for that board is loaded. In order to compare a newly manufactured Test Board, it is placed in the precision board holder in the same manner as the Golden Board and the imaging sequence is started. The camera moves through the 16 slices, according to the example above, stops at each position, and animates between the Golden Board and Test Board images on a color monitor for comparison. The system then moves the camera to the next slice upon a signal from the operator.

By digitizing and storing the Golden Board images, this prior art system eliminates the need for an inventory of actual Golden Boards. However, there are several remaining problems with this design. First, the board holder is a precision fixture that locates the Golden Board and the Test Board by engaging fixture pins into the tooling holes in each board. Therefore, various fixtures need to be built for different types of boards. Second, the fixturing of a board requires that it be taken off-line and placed in the fixture. This slows production. Moreover, fixturing can be difficult unless the board is already soldered and there are no loose components that can be disturbed or dropped. However, the ideal place to inspect for assembly defects is before soldering when the defects can be easily corrected. Third, due to the low resolution of the camera, an elaborate zooming and x-y camera positioning system is required. This adds complexity and can slow down system operation.

Accordingly, there is a need in the art for a vision comparison inspection system for printed circuit assemblies that overcomes the foregoing disadvantages of the prior art. What is required is a system that allows rapid and efficient inspection of circuit board assemblies in a production line environment without the need for time-consuming fixture set ups and complicated camera zooming and x-y positioning manipulations.

BRIEF SUMMARY OF THE INVENTION

A vision comparison inspection system is provided in accordance with the present invention that solves the foregoing problems and provide an advance in the printed circuit assembly inspection art. The inspection system is easily incorporated into a printed circuit assembly production line having a plurality of processing locations and a conveyor system for transporting circuit assemblies between processing locations in an upstream to downstream work flow direction. In a preferred embodiment of the invention, the inspection system includes a printed circuit assembly image capture and inspection conveyor disposed in the production line. The image capture and inspection conveyor is adapted to receive printed circuit assemblies from an upstream portion of the production line and to transport the printed circuit assemblies to a downstream portion of the production line for subsequent processing. An electronic imaging device is fixedly positioned to capture an image of a printed circuit assembly positioned on the image capture and inspection conveyor at an image capture location. A lighting system is mounted for illuminating the printed circuit assembly at the image capture location. A position control system positions the printed circuit assembly at the image capture location. An imaging control system, including a programmed image processing computer, an input device, and an electronic display device, are provided for alternatingly presenting on the display device a stored image of a known good printed circuit assembly and an image of the test printed circuit assembly, whereby defects in the printed circuit assembly under test can be visually identified.

The image processing device, the lighting system, the position control system and the image processing computer can be mounted on a support cabinet that is placed at an appropriate production line location to provide an image capture station. The image capture station includes an image capture station conveyor that forms the upstream part of the image capture and inspection conveyor described above. The image capture station conveyor receives printed circuit assemblies from an upstream portion of the production line and transports them to the image capture location. The image display device and the input device can be mounted on or adjacent to an operator table that is placed downstream of the image capture station to provide an inspection station. The inspection station includes an inspection station conveyor that forms the downstream part of the image capture and inspection conveyor described above. The inspection station conveyor receives printed circuit assemblies from the image capture station conveyor and transports them to a downstream portion of the production line for further processing.

The image processing device of the inspection system is preferably a high resolution digital camera that is mounted at an upper portion of the image capture station. The resolution of the camera is sufficient to acquire a single image of an entire printed circuit board having a size of up to at least about 16×16 inches at a resolution that is sufficient to allow detailed inspection of each printed circuit component and its connections to the circuit board. In this way, the camera can remain fixed during imaging and complicated camera zooming and positioning equipment is not required. If, during the inspection mode, individual subportions of a test printed circuit assembly need to be inspected, such subportions can be viewed using image processing techniques performed by the imaging control system. More specifically, as described in more detail below, the imaging control system allows users to perform vision comparison on subportions of a test printed circuit assembly in a standard sequence wherein each subportion of the test printed circuit assembly and a corresponding subportion of a known good printed circuit assembly are alternatingly displayed, i.e., animated, for vision comparison inspection. During the standard sequence, animation between the test printed circuit assembly and known good printed circuit assembly subportions continues until the user completes vision comparison inspection on that subportion and signals for the next subportion to be displayed and animated. Users can also stop animation to view the current subportion or any other area of the test printed circuit assembly on a manual basis.

The lighting system is preferably implemented as an array of high lumen, high frequency fluorescent light fixtures arranged on each side of the image capture station, below the digital camera and above the image capture station conveyor, for illuminating a printed circuit assembly positioned at the image capture location. Each light fixture includes a lower light and a upper light such that, in combination, the light fixtures provide a lower bank of low angle lights and an upper bank of fill lights. Each bank of lights is thus disposed around the periphery of an enclosed lighted area that includes the area in which a printed circuit assembly is located when it is within the field of view of the camera.

The position control system may include a retractable stop pin providing a first reference surface for engaging the leading edge of a printed circuit assembly as it is carried on the image capture station conveyor. The position control system further includes at least one clamp associated with the image capture station conveyor for clamping at least one side of the printed circuit assembly against a second reference surface. Importantly, this fixes printed circuit assemblies of all size against a common reference corner and in the same orthogonal orientation. A programmed controller is preferably provided for controlling the movement of the image capture station conveyor, the stop pin and the at least one clamp. The controller advises the imaging control system when a printed circuit assembly is positioned for imaging and is responsive to the imaging control system advising that the printed circuit assembly has been successfully imaged and can be released by the image capture station to the inspection station. The position control system controls the image capture station conveyor to stop when a printed circuit assembly is positioned for imaging and to start when imaging of the printed circuit assembly has been successfully completed.

The imaging control system preferably includes an administrative control module and a user control module. Each module is a software-based interactive processing program that interacts with production personnel through a graphical user interface presented on the output display device. The administrative control module allows an administrator to create and store images of known good circuit assemblies. To facilitate the preparation of such stored images, the administrative control module includes a mask definition function that allows an administrator to define a mask in the known good printed circuit assembly image that bounds the known good printed circuit assembly and hides extraneous image data that is outside the mask-bounded area. The mask is stored in association with the known good printed circuit assembly image in the image processing computer. It is used for clipping subsequent test printed circuit assembly images and the known good printed circuit assembly image so that only image data bounded by the mask is displayed and unnecessary image data outside the mask-bounded area is not displayed. This allows the test printed circuit assembly to be more effectively compared with the corresponding known good printed circuit assembly. If multiple palletized or panelized printed circuit assemblies are captured within a single known good circuit board image and a corresponding test printed circuit assembly image, multiple masks may be defined in the known good printed circuit assembly image to allow vision comparison of each test printed circuit assembly in the test printed circuit assembly image that is bounded by one of the masks.

The administrative control module preferably also provides a fiducial definition function responsive to input from an administrator for defining a pair of fiducials within each mask defined in the known good printed circuit assembly image and for storing the fiducials in association with the known good printed circuit assembly image in the image processing computer. The fiducials can be utilized by users to align each mask-bounded portion of the test printed circuit assembly and known good printed circuit assembly images. To provide a visual guide to administrators, each defined fiducial is designated by a fiducial mark displayed in the known good printed circuit assembly image.

The user control module is preferably adapted to automatically utilize the mask(s) defined in connection with the known good printed circuit assembly image to clip the mask-bounded portion(s) of the test printed circuit assembly image and the known good printed circuit assembly image. The user control module also preferably provides a user-assisted alignment function wherein users are allowed to place fiducials in the mask-bounded portion(s) of the test printed circuit assembly image. The fiducials placed in the test printed circuit assembly image are matched by the user control module with the fiducials previously defined by an administrator for the corresponding known good printed circuit assembly. This brings the mask-bounded portion(s) of the test printed circuit assembly image into alignment with the corresponded mask-bounded portion(s) of the known good printed circuit assembly image. The user control module may also provide a defect log function responsive to input from the user for generating a log of defects found in the test printed circuit assembly. If any such defects are identified, the system requires the user to specify how the defect has been resolved or the test printed circuit assembly will not be released from the inspection station. Optionally, the user may be prompted to identify the source (i.e., production line location) of the defect. After the user has resolved all defects, and has released the test printed circuit assembly from the inspection station, the defect log, along with other useful information, is stored in a defect log file containing records corresponding to the just-inspected printed circuit assembly under test, along with records for other printed circuit assemblies that have been tested. There can be one or more of such defect log files, with each log file preferably storing records of circuit assemblies tested over some time period, such as one month. The defect log files can specify a variety of information for each printed circuit assembly under test, including but not limited to, (1) the printed circuit assembly name or number, (2) a directory path and filename for the printed circuit assembly is stored, (3) a user identifier, a (4) defect type identifier, a (5) defect source identifier, a (6) defect resolution number, a (7) defect location (e.g., pixel coordinates) relative to a known reference point on the printed circuit assembly, and (4) date and time stamps. Optionally, defect logging can be disabled if desired.

The graphical user interface provided by the administrative and user control modules provides a menu-driven display that allows administrators and users to rapidly view and manipulate printed circuit assembly images on the output display device. In both the administrative and user modes a large primary window is provided for displaying an entire printed circuit assembly, or a sub-portion thereof, in one view. An overview window is provided adjacent to the primary window which displays a thumbnail view of the entire printed circuit assembly overlaid with a rectangular view frame illustrating the size and position of the currently-viewed printed circuit assembly sub-portion. Viewing a printed circuit assembly sub-portion in the primary window allows for detailed viewing and is the most common mode in which printed circuit assemblies are inspected for defects.

A user can quickly cycle through each image sub-portion using the standard viewing sequence referred to above. After the standard sequence has completed, users can select sub-portions manually, for example, by moving the view frame around in the overview window. If necessary, the user can also zoom in or out, pan around and scroll within the primary window in order to inspect any desired area of the test printed circuit assembly. If defects are identified during the user mode, a defect list box is preferably created adjacent to the primary window. As defects are tagged in the primary window, one or more pop-up menus appear that request the user to specify the nature of the defect, its source, and its resolution, as referred to above. Both the defect and resolution information are displayed in the defect list box. A defect tag icon is also placed in the image displayed in the primary window over the component that the user identified as being defective. The color of this icon signifies defect resolution status.

BRIEF DESCRIPTION OF THE SEVERAL VIEWS OF THE DRAWING

The foregoing and other features and advantages of the invention will be apparent from the following more particular description of a preferred embodiment of the invention, as illustrated in the accompanying Drawing, in which.

DETAILED DESCRIPTION OF THE INVENTION

Figure 1:
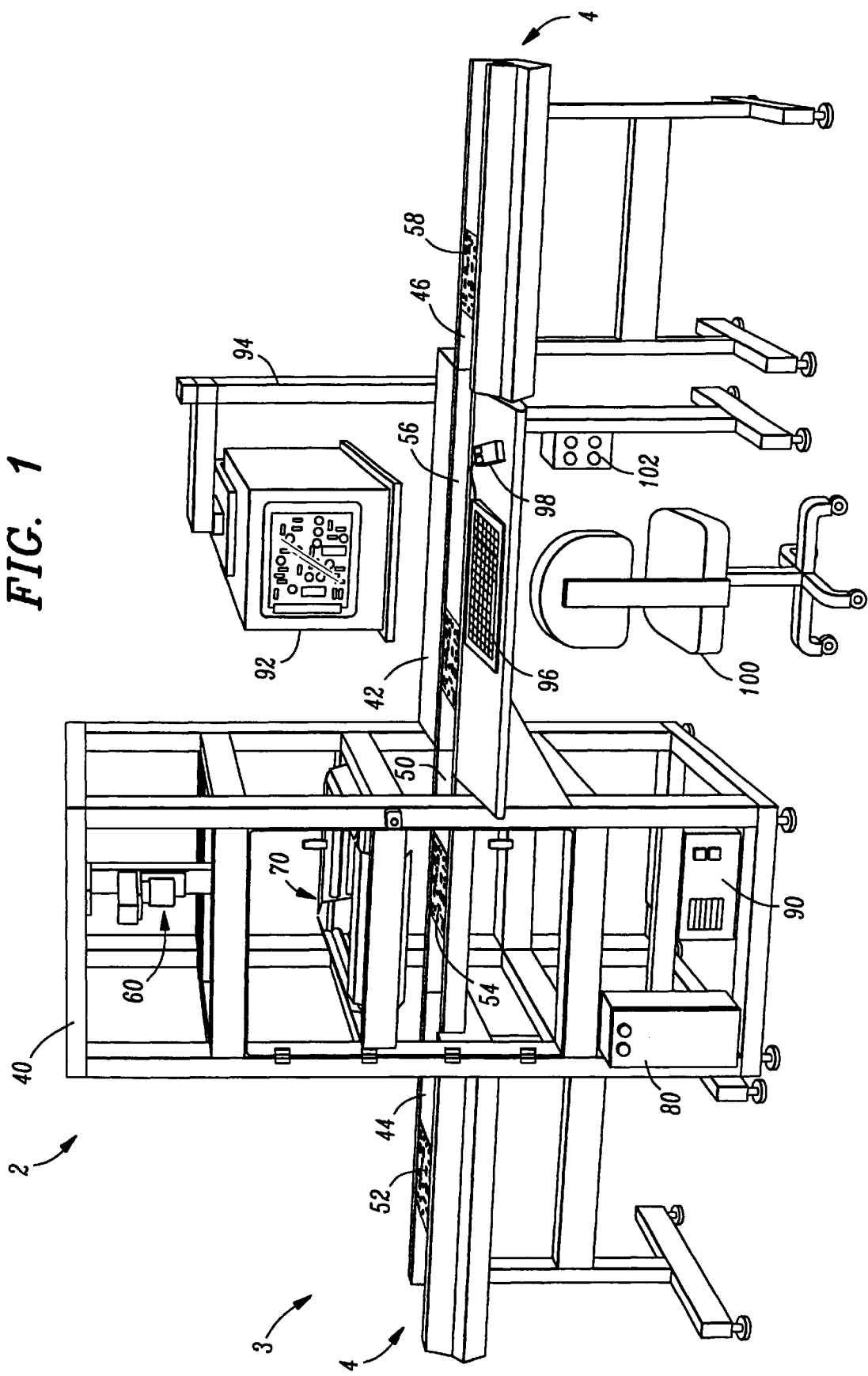
FIG. 1 is a perspective view of a vision comparison inspection system constructed in accordance with the present invention and installed as an image capture station and an inspection station in a printed circuit assembly production line.

Turning now to the Drawing, wherein like reference numbers designate like elements in all of the several views, FIG. 1, illustrates a vision comparison inspection system 2 constructed in accordance with a preferred embodiment of the invention. The inspection system 2 is intended for use in a printed circuit assembly production line 3 having a plurality of processing locations (described below with reference to FIG. 2) and a system of conveyors 4 ("conveyor system") for transporting circuit assemblies between processing locations in an upstream to downstream work flow direction. The inspection system 2 is incorporated into the production line 3 in order to inspect printed circuit assemblies for defects introduced during the installation of components at the various processing locations. As used herein, a "processing location" can be a discreet machine, an operator station or a production line sub-segment that includes plural machines and/or operator stations devoted to a single processing function or to closely related processing functions. As further used herein, the conveyor system 4 may include discrete conveyor belt assemblies that are arranged in end-to-end relationship so as to be physically adjacent to each other as well as functionally adjacent from a process flow perspective, such that printed circuit assemblies pass automatically from one conveyor to the next. The conveyor system 4 may also include conveyor assemblies that are functionally adjacent from a process flow perspective, but are physically separated, such that printed circuit assemblies must be manually transported from one conveyor to the next, for example, on a work cart or other conveyance.

Figure 2:
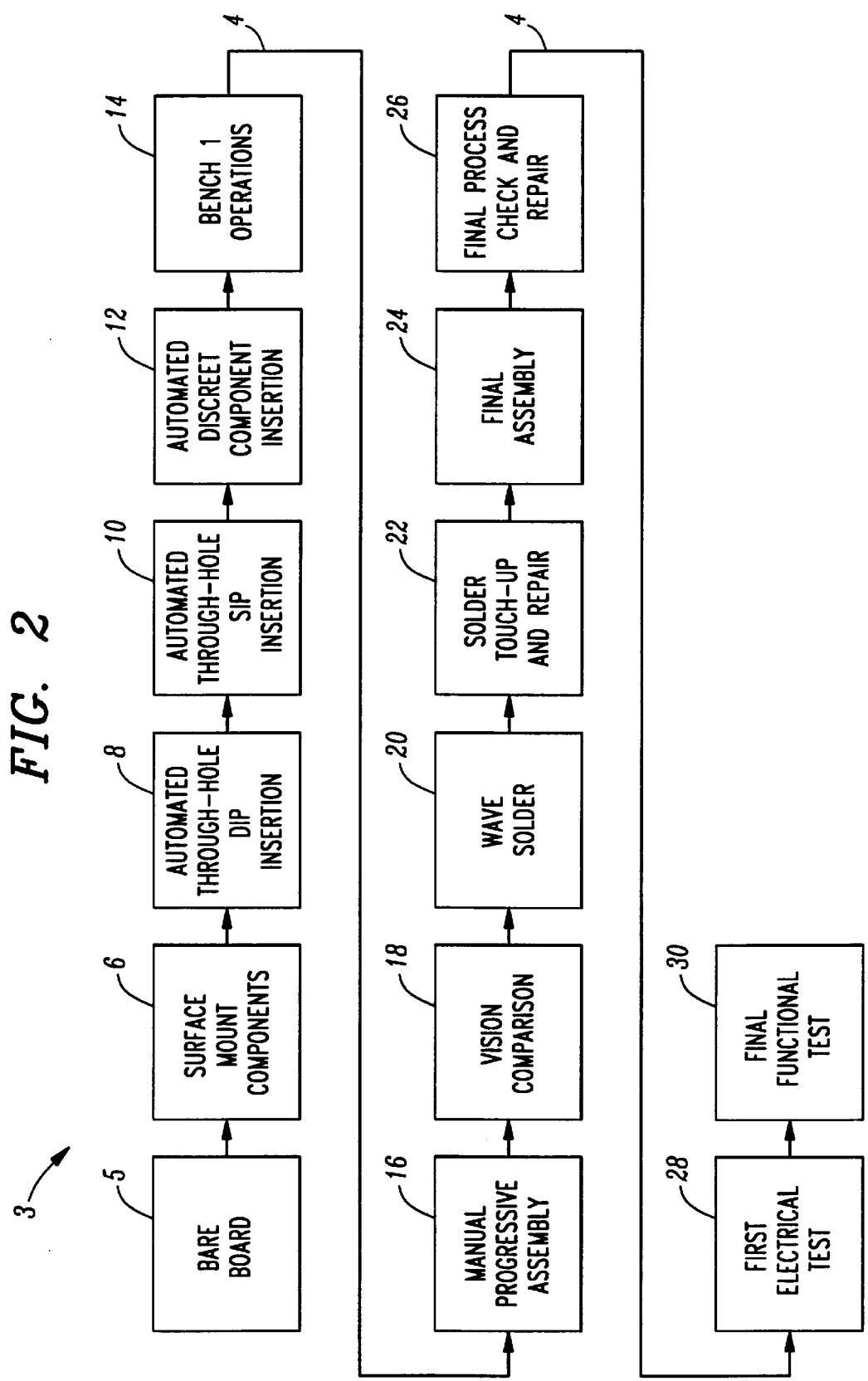
FIG. 2 is a block diagram showing a production line having plurality of production line processing locations including a processing location representing the vision comparison inspection system of FIG. 1.

As shown in FIG. 2, the production line 3 may include one or more discreet processing locations 6 through 28 positioned along the conveyor system 4, each of which, save for the vision comparison inspection location 18 of the present invention, performs a conventional production function. The processing locations 6 through 28 contribute to the assembly of finished printed circuit assemblies by performing their respective functions on each printed circuit assembly as it is carried past each processing location in a predetermined sequence. By way of example, the production line 3 could be configured in the manner now to be described. Starting with a bare printed circuit board at a process commencement point 5, a first processing step performed at processing location 6 is the automated assembly of surface mounted components on the top and/or bottom side of the bare printed circuit board. A second processing step performed at processing location 8 is the automatic insertion of through hole DIP (Dual In-line Package) Integrated circuits. A third processing step performed at processing location 10 is the automatic insertion of SIP (Single In-line Package) components such as resistor networks. A fourth processing step performed at processing location 12 is the automatic insertion of discreet components from tape reels, such as resistors, capacitors, diodes, etc. A fifth processing step performed at processing location 14 includes semi-automatic "Bench-1" operations involving manual assembly and soldering of certain components and wiring that can not be automated as above but must be secured prior to the next step. A sixth processing step performed at processing location 16 is the manual progressive assembly of components that can not be automated but do not yet have to be cut, clinched or soldered. This processing location can have varying number of individuals inserting various components in a production line sub-segment of the conveyor system 4 known as the progressive assembly line. The seventh processing step performed at the processing location 18 is the vision inspection of printed circuit assemblies in process using the inspection system 2 of the present invention. The inspection system 2 is placed at the end of the progressive assembly line 16, before the printed circuit assemblies go into a wave solder machine representing an eighth processing step performed at processing location 20. The wave solder machine solders all the installed components to the printed circuit board on which they are mounted. After wave soldering, the printed circuit assemblies proceed through a ninth processing step of solder touch-up and repair performed at the processing location 22. The tenth processing step performed at the processing location 24 is the final assembly of components such as latches and connectors that can not pass through the wave solder machine. The eleventh processing step performed at processing location 26 is final process checking and repair. The twelfth processing step performed at processing location 28 is the first electrical test. The thirteenth and final processing step performed at processing location 30 is the final functional test.

During the course of production line operations, any of the defects described above, namely, wrong components, reversed components, broken components, mis-wired components or wire jumpers, and other defects, can be introduced into the printed circuit assemblies. The basic purpose of the vision comparison inspection system 2 of the present invention is to assist the visual inspection of the printed circuit assemblies to identify and resolve such defects prior to the wave soldering operation, when defect resolution is least costly.

Returning now to FIG. 1, it will be seen that the inspection system 2 is installed directly in the production line 3 as part of the conveyor system 4. By way of overview, the inspection system 2 includes a image capture station 40 and an adjacent inspection station 42 interposed between respective upstream and downstream portions 44 and 46 of the conveyor system 4. The image capture station 40 includes a framework 41 of horizontal and vertical trusses made from aluminum or other suitable material. This framework 41 can be configured in variety of shapes and sizes, and is shown by way of example in FIG. 1 as being vertically elongated and having a generally square cross-sectional shape when viewed along its vertical axis (as also shown in FIGS. 3 through 6). An image capture station conveyor 50 is installed in the image capture station 40 using conventional mounting components that secure the conveyor 50 to the image capture station framework 41. The image capture station conveyor 50 is adapted to receive printed circuit assemblies, such as the printed circuit assembly 52, from the upstream portion 44 of the conveyor system 4 and to convey them to an image capture location within the image capture station 40 as a printed circuit assembly under test 54 (hereinafter "Test Board"). After image capture, the image capture station conveyor 50 carries the Test Board 54 downstream and hands it off to an inspection station conveyor 56 mounted on or adjacent to the inspection station 42. This allows a user to manually inspect and/or repair the Test Board 54 once it leaves the image capture station 40. The inspection station conveyor 56 is adapted to receive the Test Board 54 from the image capture station conveyor 52 and, when inspection is complete, to transport it to the downstream portion 46 of the conveyor system 4 for subsequent processing, as shown at 58.

A high resolution digital camera 60 (described in more detail below) is mounted to an upper portion of the image capture station framework 41, above the image capture station conveyor 50, for capturing an image of the Test Board 54 positioned at the image capture location. An array of high frequency fluorescent lights 70 (described in more detail below) is arranged on each side of the image capture station framework 41, below the digital camera 60 and above the image capture station conveyor 50, for illuminating the Test Board 54 when it is positioned at the image capture location. A position control system, which includes a programmed controller 80, is disposed in the image capture station 40 for positioning the Test Board 54 at the image capture location. An imaging control system includes a programmed image processing computer 90 ("imaging computer") disposed in the image capture station 40. It also includes a video display monitor 92 mounted on or adjacent to the inspection station 42 by a framework 94, and one or more input devices such as a keyboard 96 and mouse 98. The user sits in a chair 100 during inspection operations. A control panel 102 provides override controls that allow the user to start and stop the inspection station conveyor 56, to release a test board therefrom, and to by-pass inspection altogether. The controller 80 in the image capture station 40 provides similar override functionality.

Turning now FIGS. 3–6, the image capture station 40 and its components are shown in more detail. The image capture station conveyor 50 is a preferably conventional printed circuit assembly production line conveyor unit. It supports the Test Board 54 on a pair of parallel conveyor belts 110 and 112, each of which is carried by an upstream support pulley 114 and a downstream support pulley 116 (shown in FIGS. 4–6) mounted on respective horizontal rail members 118 and 120. The rail member 118 and 120 are secured to the framework 41 in conventional fashion.

Figure 3:
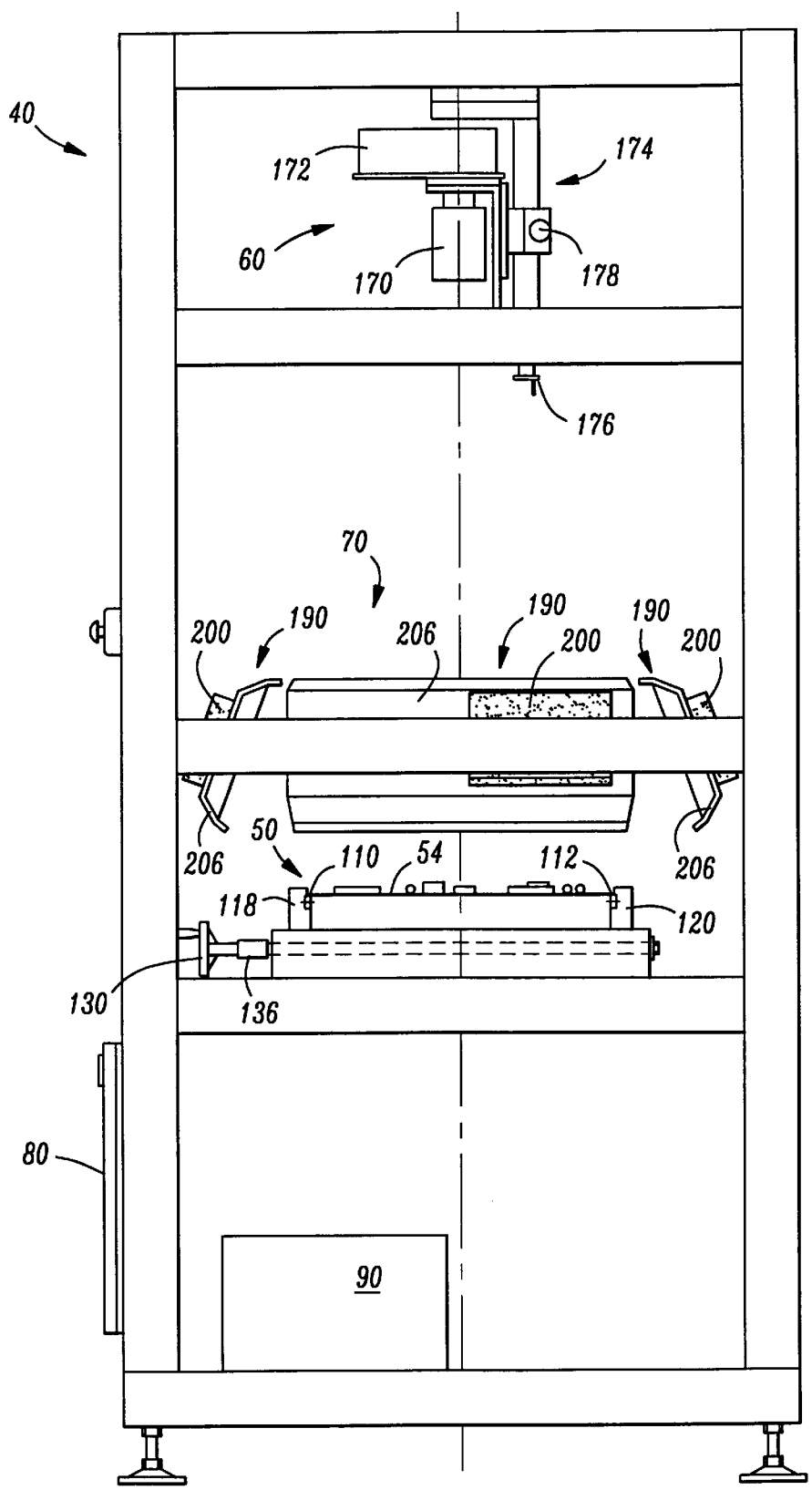
FIG. 3 is a right-side elevation view of the image capture station of FIG. 1 looking along the axis of a production line conveyor.
Figure 4:
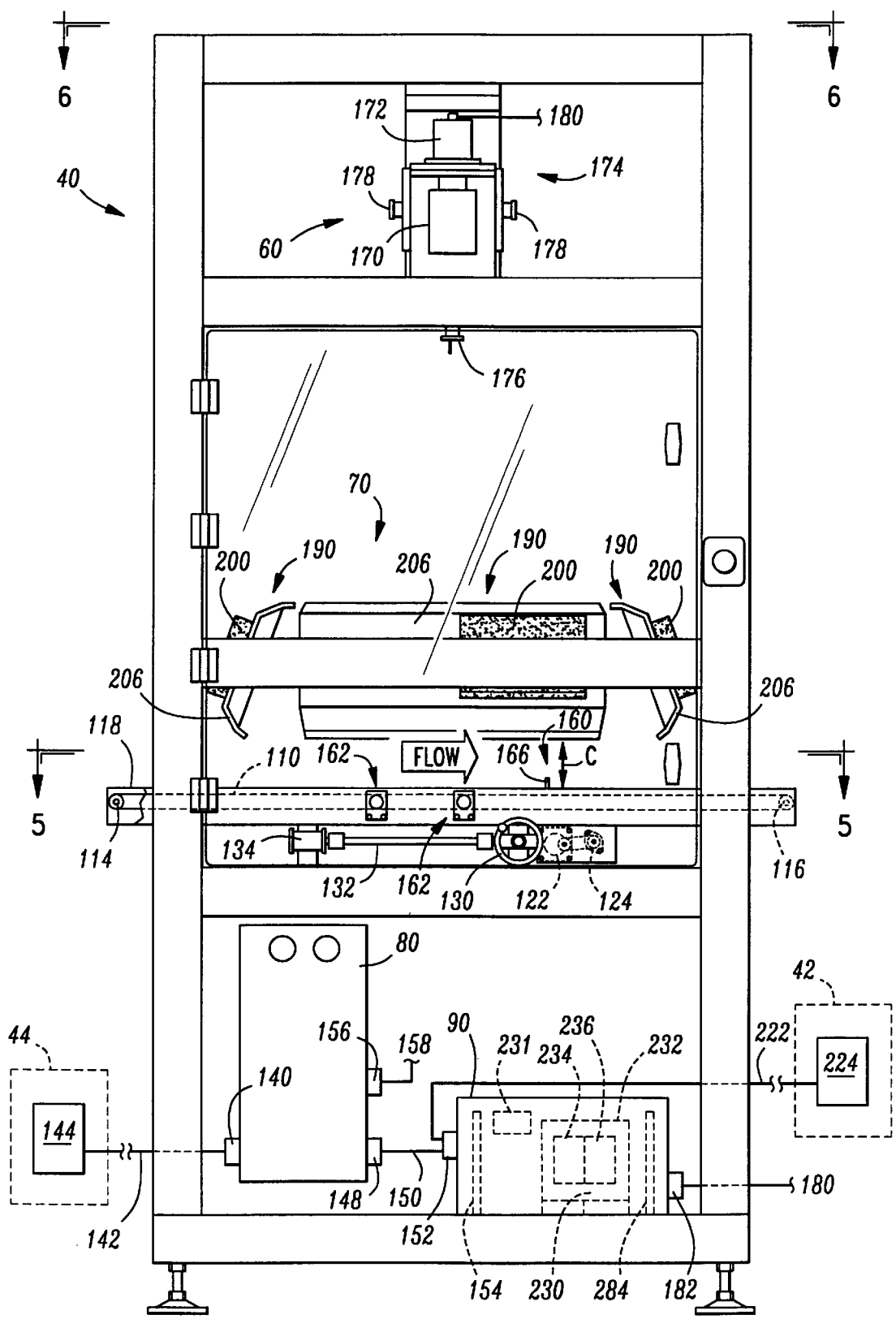
FIG. 4 is a front elevation view of the image capture station of FIG. 1 looking at the side of a production line conveyor.
Figure 5:
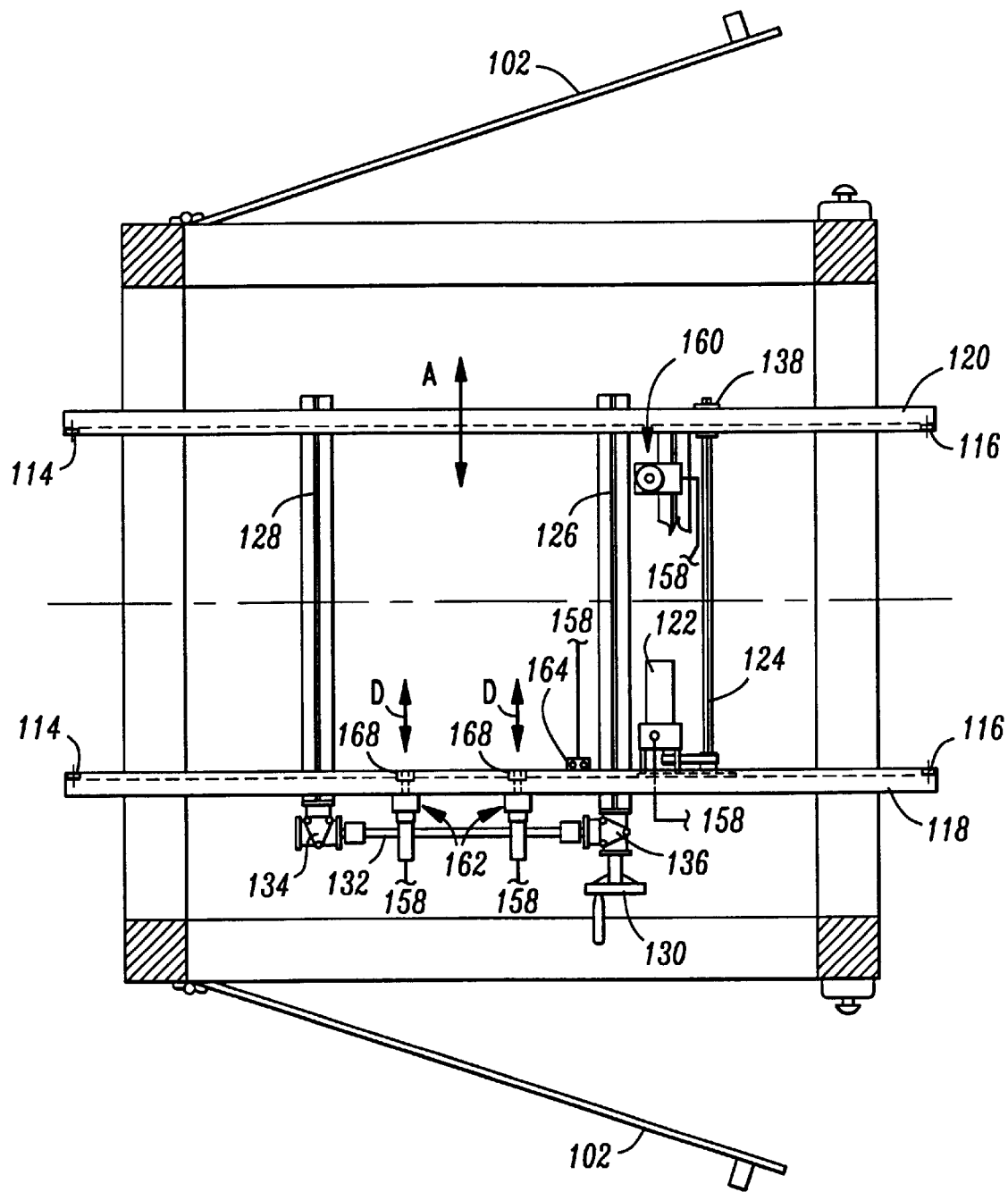
FIG. 5 is a cross-sectional view of the image capture station of FIG. 1 taken substantially along line 5—5 in FIG. 4.

As shown in FIGS. 4 and 5, a motor 122 is coupled to a drive link 124 to power the conveyor belts 110 and 112 for synchronous conveyor movement. Alternatively, individual drive motors could be used. As is also conventional, one or both of the rails 118 and 120 are preferably adjustably positionable relative to each other. In the construction of FIGS. 3–6, the rail 118 is fixedly supported on the framework 41 of the image capture station 40 while the rail 120 is movably mounted so that it can be laterally adjusted in the direction of the double-headed arrow labeled "A" shown in FIG. 5. This allows a operator to change the spacing between the rails 118 and 120 to accommodate work pieces of different size. The rail 120 can be adjusted in a variety of ways. In the construction of FIGS. 3–6, the rail 120 is adjusted with a pair of adjustment screws 126 and 128. The adjustment screw 126 is attached to a crank 130 that is readily accessible to a operator. A drive link 132 drivably connects the adjustment screw 126 to the adjustment screw 128 by way of gear coupling units 134 and 136. A sleeve connection 138 allows the rail 120 to move relative to the drive link 124 as the rail 120 is adjusted. Many other rail adjustment schemes could also be used, or in the alternative, rail adjustments could simply be eliminated.

Figure 6:
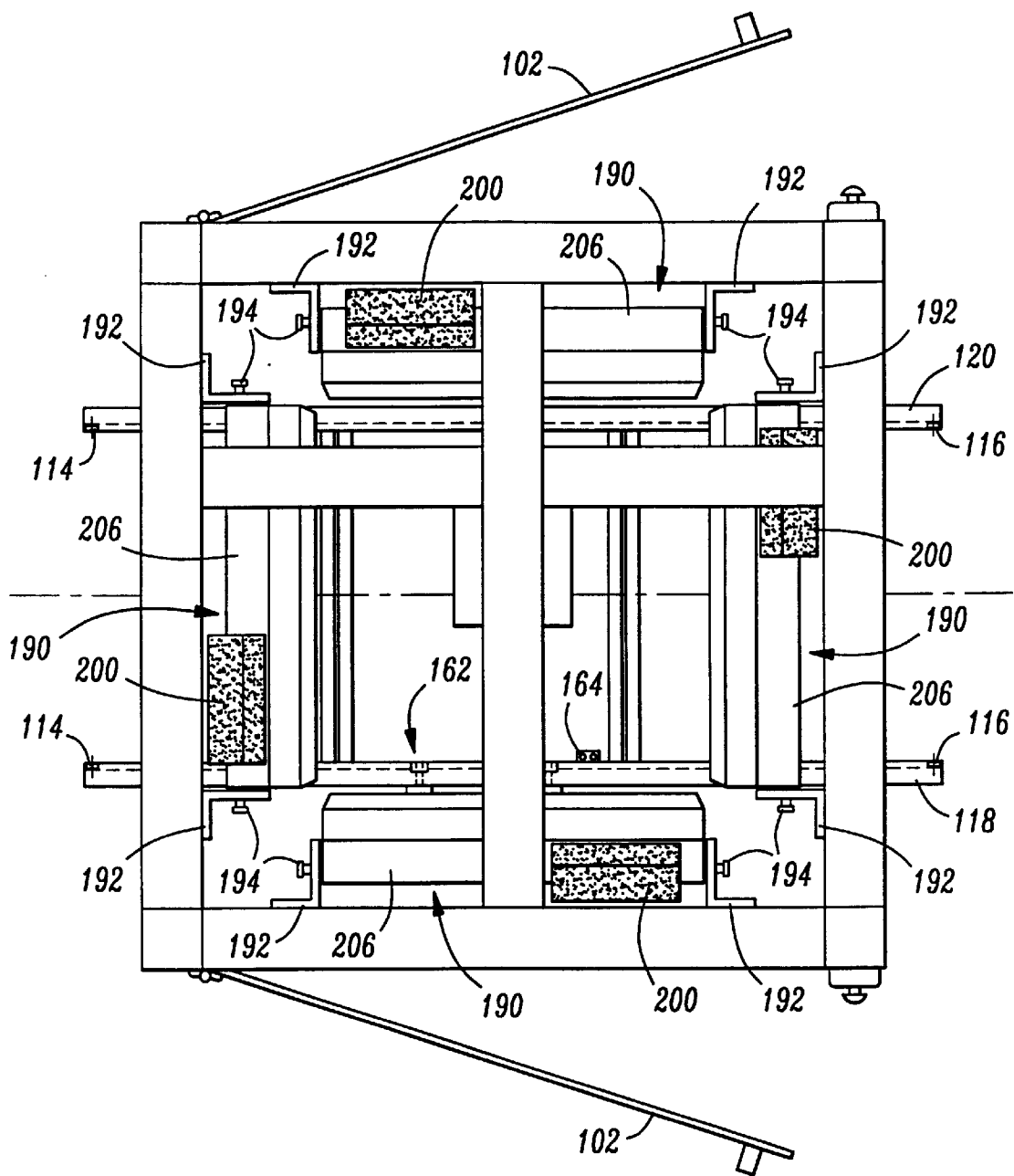
FIG. 6 is a top view of the image capture station of FIG. 1 looking substantially in direction of line 6—6 in FIG. 4.

As briefly described above, the position control system used to position a Test Board at the image capture location within the field of view of the digital camera 60 includes a programmed controller 80, which is further illustrated in FIGS. 3 and 6. The controller 80 is a conventional programmable logic control device ("PLC") that is programmed via conventional relay ladder logic or equivalent to receive electrical inputs from sensors and other input devices and to provide appropriate outputs to solenoids, switches and other output devices. Connectors configured in accordance with the SMEMA ("Surface Mount Equipment Manufacturers Association") Electrical Equipment Interface Standard may be used for coupling the controller 80 to the input and output devices. Three such connectors are used in conjunction with the controller 80.

Referring now to FIG. 4, a first connector 140 provides the usual communications between the controller 80 and the upstream conveyor portion 44 via a control cable 142. More particularly, the controller 80 communicates with a counterpart controller 144 associated with the upstream conveyor portion 44. The controller 144 is programmed to hold the Test Board 52 at a position determined by an optical sensor (not shown) in the upstream conveyor portion 44, and does not advance the Test Board 52 to the image capture station 40 until the controller 80 signals that the Test Board 52 may enter the image capture station 40.

A second connector 148 provides communication between the controller 80 and the imaging control system computer 90 via a control cable 150 and a computer-mounted connector 152. More particularly, the controller 80 provides an output to the imaging computer 90 that a Test Board is ready for image capture. Conversely, the controller 80 receives an input from the imaging computer 90 to release the Test Board 54 after an image has been successfully captured. A standard isolated input/output interface card 154, such as a PDISO-8 board or equivalent, is installed in the imaging computer 90 to communicate with the controller 80. The connector 152 is, by way of example, a DB-37 female connector.

A third connector 156 provides communication between the controller 80 and additional components of the position control system now to be described, via control cables 158. The additional components of the position control system are mounted on the image capture station framework 41 and comprise, as shown in FIGS. 4 and 5, a solenoid actuated pneumatic stop cylinder unit 160, a plurality of solenoid actuated pneumatic clamp units 162 (two of which are shown in FIG. 5), and an optical sensor 164. The stop cylinder unit 160 is a conventional pneumatically-driven production line hold-and-release mechanism. It includes a cylindrical shaft 166 that is retractable and extendable in the direction of the double-headed arrow labeled "C" in FIG. 4. A solenoid, not shown, provides pressurized air to the stop cylinder unit 160 in response to a control signal provided over one of the control cables 158 to the solenoid. The clamp units 162 each include a pneumatically-driven clamp 168 formed as a movable segment of the rail 118 (or the rail 120) so as to be extendable and retractable in the direction of the double-headed arrows labeled "D" in FIG. 5. A solenoid, not shown, provides pressurized air to the clamps 168 in response to a control signal provided over one of the control cables 158. The optical sensor 164 is conventional in nature. It communicates with the controller 80 via one of the control cables 158 and produces a signal in response to a circuit board passing overhead.

The foregoing elements of the position control system operate in the following manner. The Test Board 54 is conveyed by the conveyor belts 110 and 112 in the direction of the arrow labeled "FLOW" in FIG. 4. As the leading edge of the Test Board 54 passes over the optical sensor 164, the optical sensor alerts the controller 80 and the controller 80 sends a signal to the drive motor 122, which is also connected to the controller 80 via one of the control cables 158. The controller 80 signals the drive motor 122 to shift to a slower speed to control the impact of the Test Board 54 on the stop cylinder shaft 166, which the controller 80 has previously signaled to extend to its board engagement position. A timer in the controller 80 stops the conveyor motor 122 within seconds after the leading edge of the Test Board 54 engages the stop cylinder shaft 166. At this time, the controller 80 activates the clamping units 168 to extend the clamps 168 to clamp the Test Board 54 against the fixed rail 120. The controller 80 then signals the imaging computer 90 that the Test Board 54 is positioned at the image capture location and ready for imaging. Importantly, this action clamps the same corner of all sizes of printed circuit assembly boards to the same reference point, which is the corner of the board defined by the edge that abuts against the rail 120 and the edge that abuts against the stop cylinder shaft 166. Preferably, this corner corresponds to a reference corner of the field of view of the camera 60.

As shown in FIGS. 3 and 4, the camera 60 is a system that includes a lens arrangement 170 and a housing 172 containing the camera electronics. The camera 60 is mounted on a manually adjustable optical mounting assembly 174 that is secured to an upper portion of the image capture station framework 41. The mounting assembly 174 allows the camera 60 to be vertically positioned to the required height above the Test Board 54. Adjustment knob 176 is provided for making vertical position adjustments. The knobs 178 are provided for clamping the vertical position of the camera 60. Importantly, once these adjustments are made, the digital camera 60 remains stationary, i.e., fixedly positioned, at the same location during all phases of the inspection procedure and for all printed circuit assembly sizes. As shown in FIG. 4, the camera is attached to an electrical control and data cable 180 that attaches to a connector 182 on the imaging computer 90. The control and data cable 180 transmits control signals from the imaging computer 90 to the camera 60 and image signals from the camera 60 to the imaging computer 90. An image capture card 184 is installed in the imaging computer 90 for processing the image from the camera 60.

It has been determined by experiment that an image resolution representing 120 dots per inch of a printed circuit assembly provides enough resolution to enable detailed inspection of the printed circuit assembly on a conventional video monitor, such as the display device 92 (see FIG. 1). Markings on most components at this resolution are generally readable. With that consideration, the digital camera 60 preferably has a resolution of at least about 2000×2000 pixels. This is sufficient to provide a resolution of 120 dots per inch over a field of vision of 16.66×16.66 inches, which is adequate for most printed circuit boards. The advantage of implementing the digital camera 60 as a high resolution device is that for circuit boards of all sizes, there is no need to zoom or pan the digital camera 60 over the board, or to move the board relative to the camera. Although in many cases a large amount of resolution can be wasted, the simplicity of the mechanical implementation outweighs the potential for wasted resolution.

In order to cover the 16×16 in. field of view, provide adequate depth of focus and minimal geometric distortion, a proper mounting height and lens must be chosen for the digital camera 60. The lens must be of high optical quality and is preferably zoomable, for purposes of initial alignment only. One suitable camera for this application is the "T2 High Resolution CCD Video Camera" from Megavision Inc. of Santa Barbara, Calif. This CCD ("Charged Coupled Device") camera has a resolution of 2000×2000 pixels. Importantly, the T2 camera has a large dynamic range such that even with detail in dark areas, the bright areas such as those from specular reflections are not saturated. Another issue with respect to CCD cameras is the blooming phenomenon. If a pixel is saturated due to too much light, the charge from this pixel can leak into adjacent pixels. The T2 camera uses deep well CCD structure to minimize blooming. The T2 camera also provides a true 4 million pixel resolution with 24 bits color. That is because it has a monochrome CCD but captures three images using red, green, and blue filters in sequence. These three color images are mixed to form a composite color image. Preferably, a Micro Nikor F2.8 lens is used to match the T2 camera to the imaging application of the present invention.

The lighting system 70 is designed to provide uniform diffuse light over a field of view that encompasses 16 in.×16 in. The vision comparison system 2 handles many types and sizes of boards with varying shapes and sizes of components. Many devices, such as integrated circuits, have their logos and device designations applied with laser-etching, which is difficult to see, even by the naked eye, with high-angle top lighting. Such components are best viewed with low-angle lighting that produces shadows in the etched lines. On the other hand, tall components can cause shadows over other components and parts of the board if viewed with a very low angle of lighting. Consequently, fill lighting also provided, as described in more detail below. The color temperature of the light is also important because it has to be matched to the spectral sensitivity of the camera. The amount of available light flux has to be sufficient to allow a low enough aperture opening on the camera for a respectable depth of field. By way of example, in the imaging application of the present invention, the target aperture can be set to F-11. This provides a depth of focus that is large enough (e.g., up to at least about one inch) to image all of the components of a Test Board 54, which can reach as high as one inch or more above the circuit board surface.

In order to cover a field of view of 16 in.×16 in., the lighting system 70 is implemented using four two-lamp fluorescent fixtures 190 that are mounted to the image capture station framework 41 in a square configuration, as shown in FIGS. 3, 4 and 6. As shown in FIG. 6, each fixture 190 is mounted to the framework 41 using a pair of L-shaped brackets 192. The fixtures 190 are attached to the brackets 192 using thumb-screws 194 which extend through slots (not shown) in the brackets 192, such that the fixtures 190 are rotatable about the axes of the thumbscrews and transversely positionable within the slots.

Figure 7:
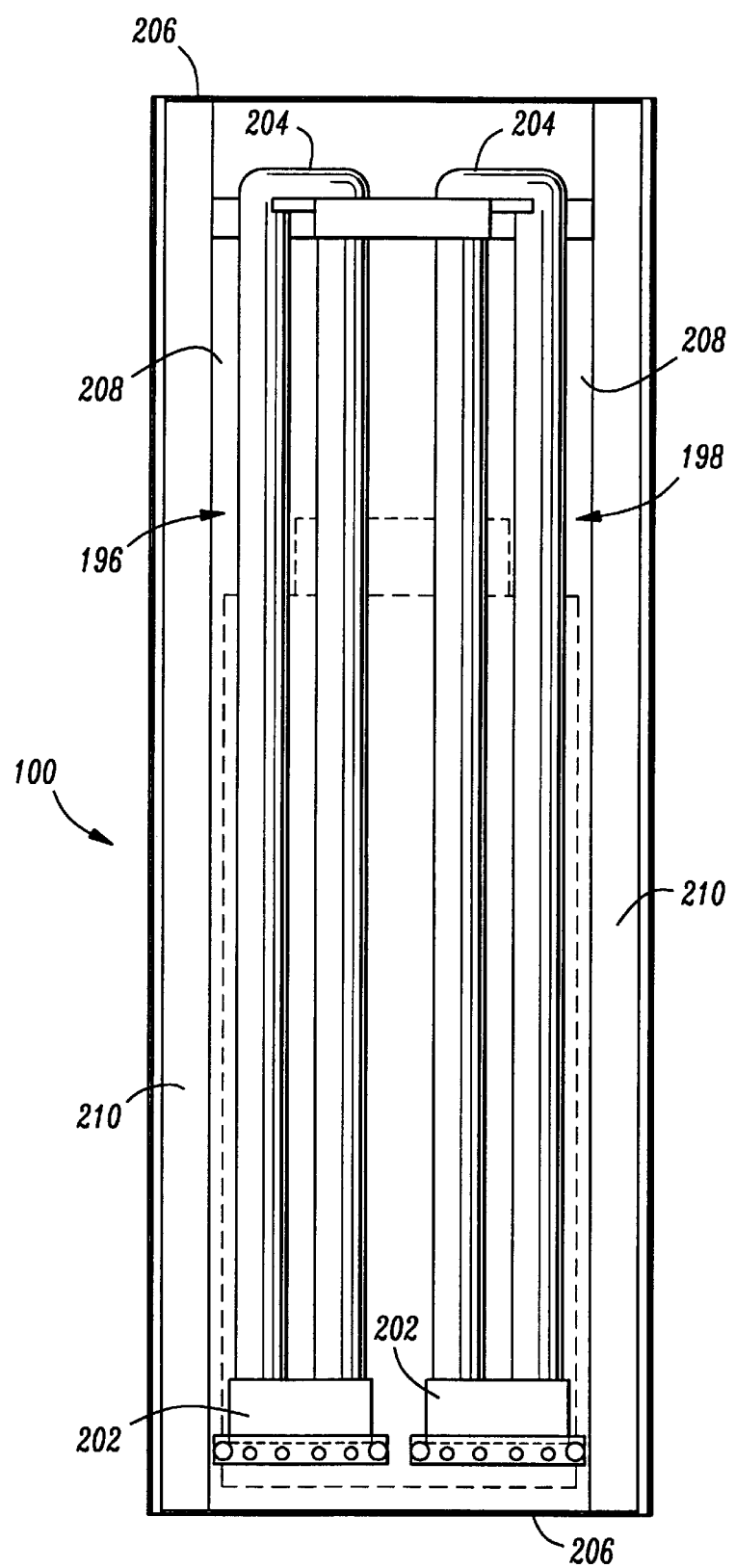
FIG. 7 is a bottom view of one of four lighting fixtures used in the vision comparison inspection system of FIG. 1.
Figure 8:
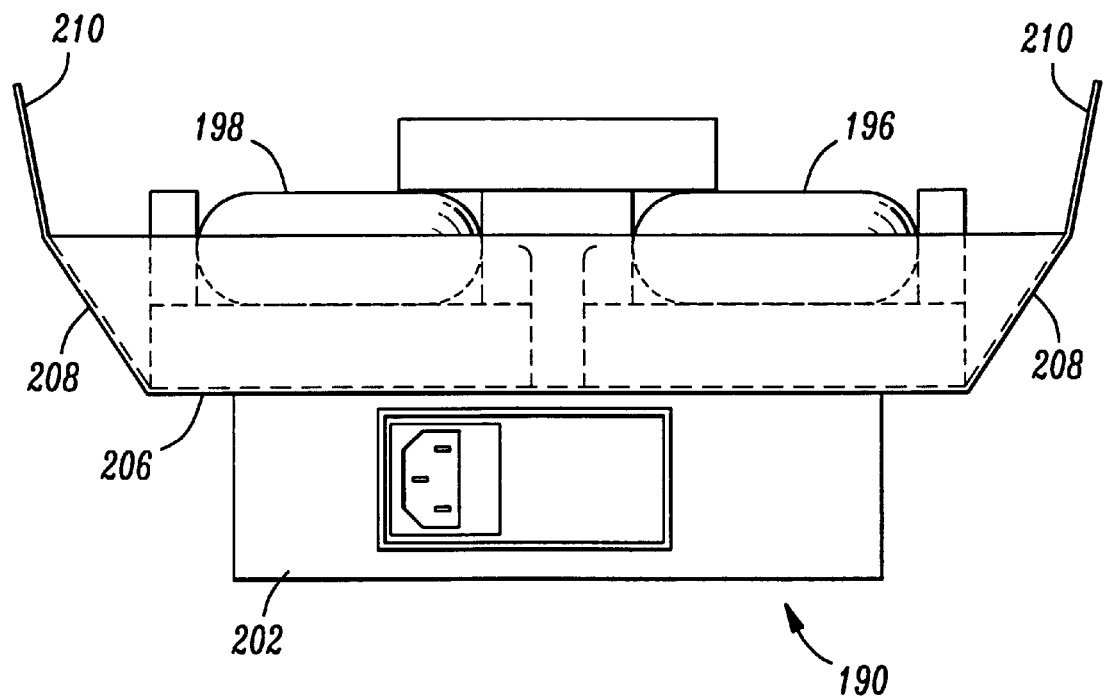
FIG. 8 is an end view of the lighting fixture of FIG. 7.

As further shown in FIGS. 7 and 8, the fixtures 190 each use two U-shaped fluorescent lamps 196 and 198 of appropriate length (e.g., 24 inch long). The lamps 196 and 198 are preferably very high efficiency Tri-Phosphor lamps, such as are known commercially as "High Lumen Biax" lights. They are available in several color temperatures but in the imaging application of the present invention, a color temperature of 5000 K was chosen to match the spectral needs of the T2 camera 60. In order to prevent flicker, a high frequency (e.g., 25 kHz) electronic ballast 200 is provided to control both of the lamps of one fixture. The lamps 196 and 198 connect to the ballast 200 through standard plug-in fluorescent lamp sockets 202. The opposite ends of the lamps 196 and 198 are supported by brackets 204.

The lamps 196, the ballast 200, the connectors 202 and the brackets 204 are all mounted on a reflector assembly 206. The lamps 196 and 198 are oriented parallel to each other with their respective longitudinal axes being separated by about 6 inches. The light-reflecting side of the reflector assembly 206 is preferably painted with semi-diffuse white satin paint. As shown in FIG. 8, the reflector assembly 206 is generally flat underneath the two lamps 196 and 198, but the side portions 208 and 210 of the reflector assembly 206 are angled to collect and direct off-axis light toward the Test Board 54 without major hot spots.

As previously mentioned, and as shown in FIGS. 3, 4 and 6, there are four light fixtures 190 mounted in the image capture station 40 in a square arrangement. The whole lighting system 70 is positioned about 10 inches above the surface of the Test Board 54. The foregoing lighting arrangement provides two banks of lights, one upper and the other lower. Each bank of lights is disposed around the square periphery of an enclosed lighted area that includes the image capture location at which the Test Board 54 is positioned when it is within the field of view of the digital camera 60. The bottom four lamps in the square representing the lower bank of lights provide very low angles of light for contrast enhancement (i.e., by shadowing component edges and identification etchings) and the top four lamps representing the upper bank of lights provide subtle amounts of fill lighting for shadow minimization or elimination (i.e., by minimizing or eliminating shadow casting from tall components). The combination of all the four light fixtures 190 provides very uniform lighting over the entire field of view. Each of the lamps 196 and 198 is preferably about 50 watts and therefore the total power of the lighting system 70 is approximately 400 watts. These lamps run relatively cool and therefore thermal problems are avoided.

The imaging computer 90 provides the core of the imaging control system that captures and displays printed circuit assembly images in accordance with the invention. Although not shown, there are standard interface cables running from the imaging computer 90 to the video display monitor 92, and to the imaging computer 90 from the keyboard 96 and the mouse 98. As shown in FIG. 4, an additional control cable 222 extends from the computer-mounted connector 152 to provide communications between the imaging computer 90 and the inspection station 42. More particularly, there is a standard controller 224 associated with the conveyor 56 of the inspection station 42. Under its program, the conveyor 56 transports the Test Board 54 after it is released from the image capture station 40 to an inspection location in front of the operator. The controller 224 will not reactivate the conveyor 56 to release the Test Board to the downstream conveyor portion 46 until the imaging computer 90, based on operator input, signals that the Test Board 54 has completed its inspection.

The functions of the imaging control system are performed by the imaging computer 90 under the operation of computer software, illustrated graphically by reference numeral 230 in FIG. 4. The computer software 230 can be written in any appropriate high level computer programming language, and is preferably written using an object-oriented language such as C++. The software 230 is most preferably written using a visual programming aid such as Visual C++ from Microsoft Corporation. The computer software 230 is rendered to machine readable form by conventional compiling and linking and is stored as one or more files on the computer 90's hard drive 231. When invoked, the computer software 230 is loaded into the program memory 232 of the imaging computer 90, preferably by an operating system providing graphics-based command and control functionality, such as Windows NT™, Windows 95™, OS/2™, or one of the various Unix flavors operating, for example, through an X Windows graphics server. Alternatively, the computer software 230 could be written to provide is own graphic controls.

As described in more detail below, there are several features of the computer software 230 that enhance the use and practicality of the vision comparison inspection system 2. The two main functions associated with the computer software 230 are (1) the administrator functions involving the creation of Golden Boards, and (2) the user functions involving the inspection of Test Boards by comparing them with Golden Board images. The administrative functions are performed by an administrative software module 234, and the user functions are performed by a user software module 236. Both modules could be written as part of a single software program, but are preferably implemented as separately executable programs. The administrative and user control modules 234 and 236 each provide a number of significant operational features. Although some of these features are common to both modules, such as image display windowing, fiducial creation, zooming, panning and scrolling functions, there are other features which are specific to each module.

The graphical user interface tools of the administrative software module 234 are shown in FIGS. 9–13, and include a main window 240 and a secondary overview window 242. As shown in FIGS. 14–23, the user software module employs the same windows 240 and 242, with the overview window being expanded to provide a defect list area 244. In each of FIGS. 9–23, the windows are formed from standard graphics components invoked using the Application Program Interface (API) provided as part of the Microsoft Windows NT™ Operating System. Other Graphical User Interface (GUI) libraries could also be used.

As will be appreciated by persons skilled in the software programming art, the graphical user interface components described herein provide an event driven software environment wherein inputs received via the interface components are processed by event handlers that perform the various functions of the invention that are assigned to them. These functions are described in detail below. It will be further appreciated that any of a variety of image processing software routines could be written to perform the described image processing functions. These image processing functions include (1) defining masks and generating mask images, (2) clipping images using mask definitions, (3) defining fiducials and generating fiducial mark images, (4) aligning images using fiducials, (5) animating images by displaying them in alternating fashion, and (6) performing various image manipulations such as zooming, panning, scrolling, and navigating through large images using image subportion view frames. No particular imaging software routines for performing such functions are preferred, and no detailed descriptions of such routines are necessary to facilitate implementation of the invention, the selection of appropriate image processing software routines for performing the functions described herein being strictly a matter of design choice.

As shown in FIGS. 9–23, the main window 242 includes a window title bar 246, a menu bar 248, a tool bar 250, a status bar 252 and a scrollable primary window 254 containing a full-size printed circuit assembly image. The overview window 242 includes a title bar 256, a viewing area 258 containing a printed circuit assembly thumbnail image. In the user mode shown in FIGS. 14–23, a scrollable defect list box 260 containing defect information is also provided.

The menu bar 248 and the tool bar 250 provide different function selections depending on whether the imaging computer 90 is executing the administrative software module 234 or the user software module 236. Functions deemed significant to the present invention are discussed below in relation to the description of operations performed by the inspection system 2 during execution of the administrative and user software modules 234 and 236, respectively.

Figure 9:
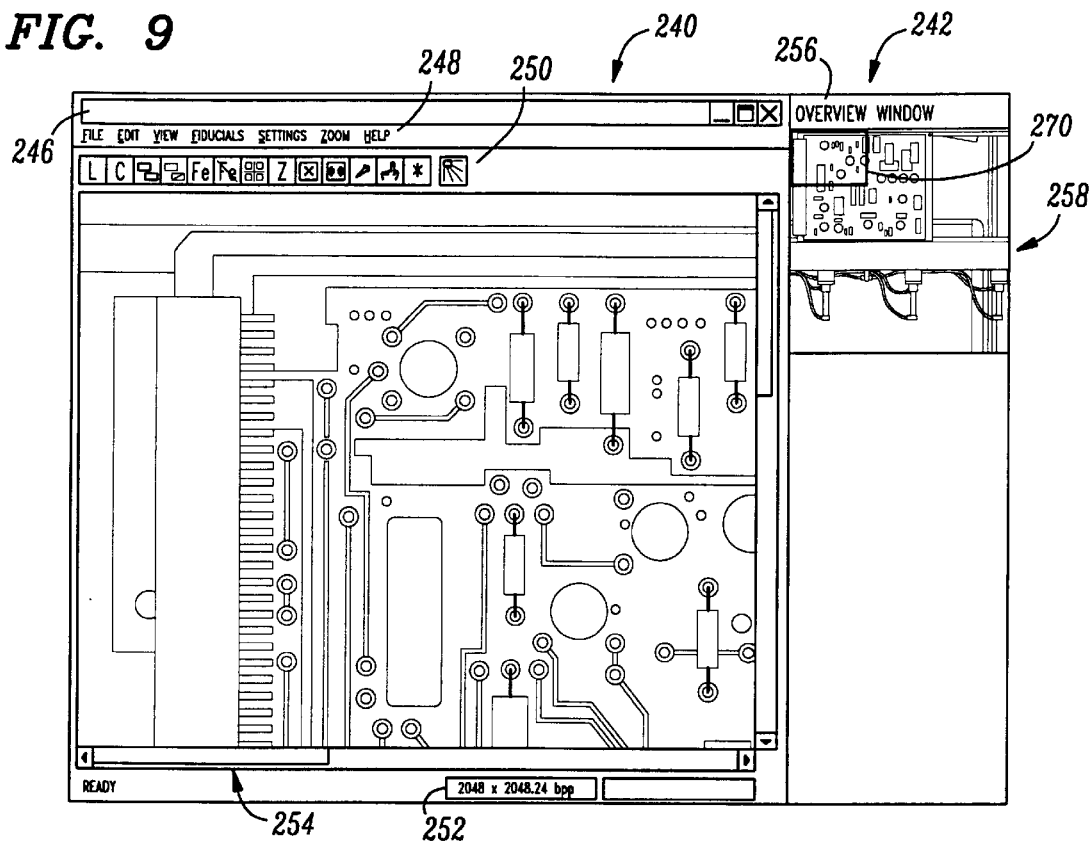
FIG. 9 is a screen-shot view showing a graphical user interface provided during an administrative session of the vision comparison inspection system of FIG. 1, in which a top left subportion of a known good printed circuit assembly is displayed in a primary window following invocation of the administrative mode and a corresponding thumbnail of an entire known good printed circuit assembly image and a superimposed rectangular view frame are shown in an overview window.

The purpose of the administrative software module 234 is to create one or more Golden Board files, or edit previously created Golden Board files, using the administrative software module 234. Although the administrator may sometimes work with a previously stored Golden Board file by calling the file up from the disk drive 231, in the usual case the administrator will capture a new Golden Board image. The administrator will thus place a Golden Board on the conveyor 50 of the image capture station 40 and activate the conveyor 50 to transport the Golden Board to its image capture location wherein the Golden Board engages the stop cylinder shaft 166 and is clamped by the clamping tabs 168 of the clamping units 162. The administrator invokes the administrative software module 234 on the imaging computer 90 and the software activates the digital camera 60 to capture a color image of the Golden Board. The captured image is shown in FIG. 9. The overview window 242 shows a Golden Board image representing everything within the field of view of the digital camera 60. It also displays a rectangular view frame 270 representing a subportion of the captured Golden Board image that is displayed in the primary window 254.

Figure 10:
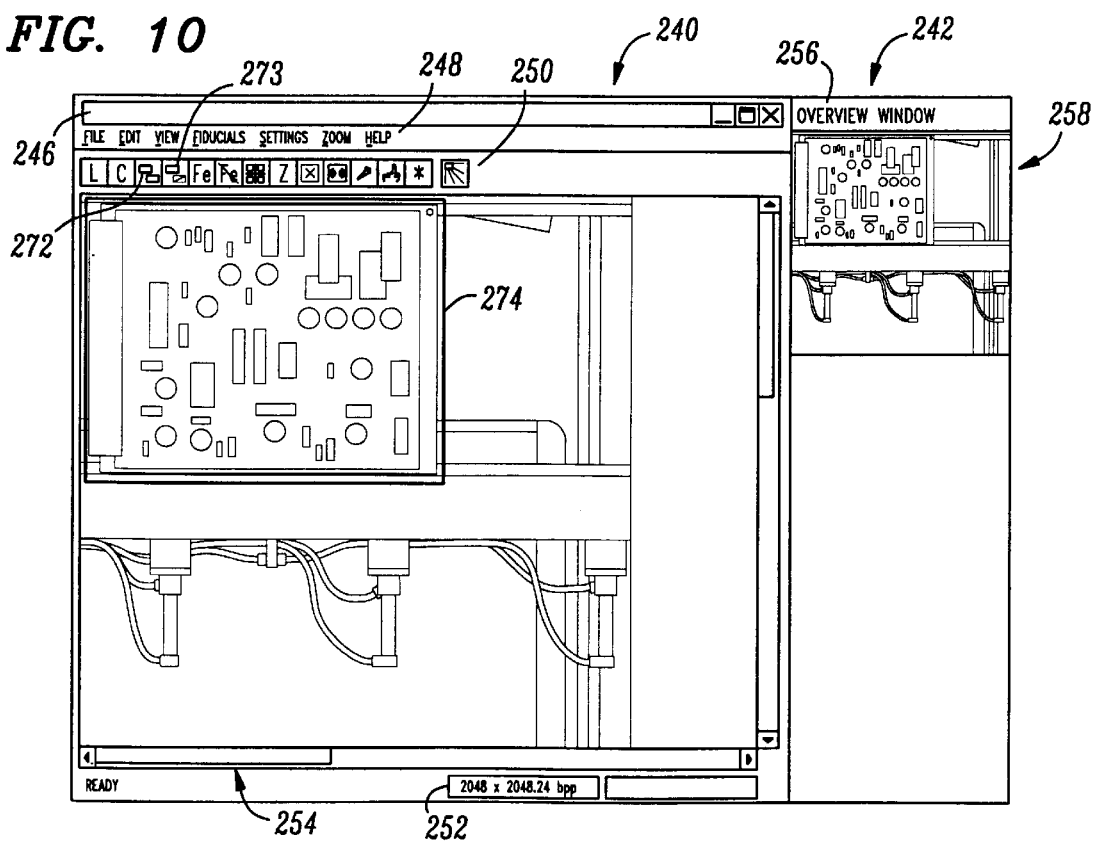
FIG. 10 is a screen-shot view showing a graphical user interface provided during an administrative session of the vision comparison inspection system of FIG. 1, in which an entire known good printed circuit assembly image with a superimposed mask outline, is presented in a primary window and a corresponding thumbnail of the entire known good printed circuit assembly image is shown in an overview window.

Because Golden Boards come in a variety of sizes, the captured Golden Board image may or may not correspond to the boundaries of the Golden Board being imaged. For that reason, the administrator is permitted to define a mask around the Golden Board. This mask is used during the user mode to clip the Test Board and Golden Board images such that only the mask-bounded portion of the Test Board and Golden Board images are displayed, while unnecessary image information outside the mask area is not displayed. If properly defined, the mask will cause only the actual Test Board and Golden Board to be shown during animation. The mask function can be invoked by selecting the Mask button 272 located in the tool bar 250 of the main window 240, as shown in FIG. 10. This selection is performed using a conventional "point and click" mouse operation with the left mouse button being clicked. When the mask button 272 is selected, the entire Golden Board image in the overview window 242, representing everything within the field of view of the digital camera 60, is displayed in the primary window 254, as shown in FIG. 10. To set the mask, the administrator positions the mouse pointer at, or slightly outside of, one corner of the Golden Board and presses the left mouse button. While still holding the left mouse button pressed, the administrator performs a conventional "drag-and-drop" operation while moving the pointer of the mouse 98 to an opposite corner of the Golden Board. As soon as the administrator begins moving the mouse 98 during the drag-and-drop operation, a mask outline 274 is displayed in the primary window 254 that enlarges as the mouse pointer is moved to the opposite corner of the Golden Board. The mask outline 274 can be enlarged until the entire Golden Board is within its boundaries. The drag and drop operation is then terminated by releasing the left mouse button. This operation sets (i.e., defines) the mask. Preferably, the mask is slightly larger than the Golden Board. If the mask is not properly defined, it can be erased using the Delete Mask button 276, shown in FIG. 10. Once the mask is set, it is saved by the software at the end of the administrative session as part of a Golden Board parameter file. As indicated, the mask is used during subsequent user mode sessions to clip the Test Board and Golden Board images so that only the mask-bounded portions of the Test Board and Golden Board images are displayed during vision comparison inspection operations. Unnecessary information outside of the mask is not displayed.

A further feature of the mask function is that multiple masks can be defined on a single captured image. This is useful for palletized circuit assemblies wherein a single pallet carries multiple circuit assemblies. These pallets resemble picture frames made of steel sides with bottom panels on which the circuit assemblies rest. The bottom panels have cutouts to expose the bottom side of the circuit assemblies to the wave soldering machine at processing location 20 (see FIG. 2). The pallets are not precision fixtures insofar as they are simply carriers for the circuit assemblies.

The pallets that hold the various types of circuit assemblies vary in size and shape, as do the circuit assemblies themselves. They may hold one or multiple circuit assemblies. This is not a concern if the pallets are always full, but that is not always the case, and multiple printed circuit assembly pallets may only be partially populated. In any event, because the digital camera 60 is positioned to capture an image of the entire pallet, it is desirable to mask off unwanted detail using the multiple masks to define areas of interest that include the circuit assemblies only. The administrative software module allows such multiple masks to be defined for use in clipping subsequent palletized Test Board and Golden Board images.

Multiple masks can also be used for panelized circuit assemblies wherein multiple copies of a small circuit pattern are repeated on the same substrate for processing efficiency. These circuit patterns are later separated at the end of production.

Figure 11:
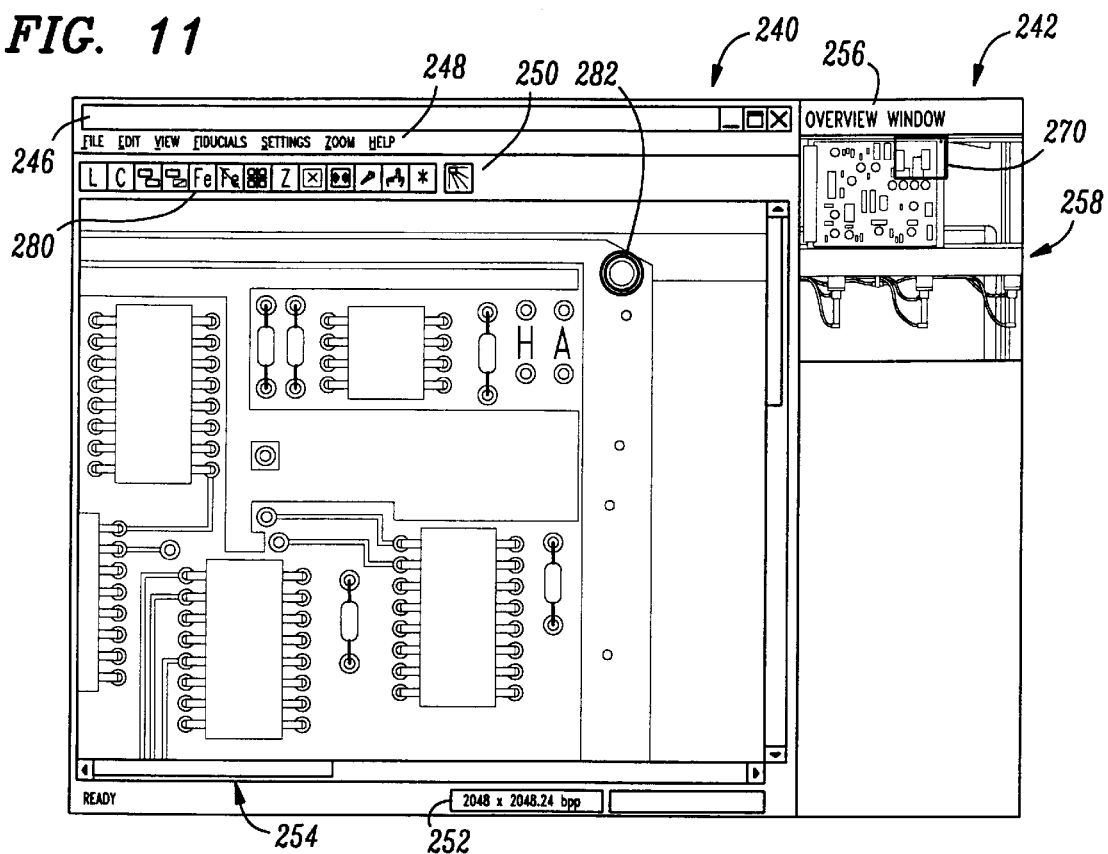
FIG. 11 is a screen-shot view showing a graphical user interface provided during an administrative session of the vision comparison inspection system of FIG. 1, in which a first zoomed area of a known good printed circuit assembly image and a target for placing a first fiducial mark therein are displayed in a primary window and a corresponding thumbnail of the entire known good printed circuit image and a superimposed rectangular view frame are shown in an overview window.

In order to facilitate the alignment of Test Board images with a Golden Board image, it is helpful to define a pair of fiducials at appropriate locations within each mask defined in a Golden Board image, such as two opposing corners of each mask-bounded portion of the Golden Board image. The fiducials are used for the user-assisted alignment of each mask-bounded portion of subsequent Test Board images if, for some reason, the Test Board images do not line up with the Golden Board image, and more particularly, if the mask-bounded portions of the Test Board images do not line up with the corresponding mask-bounded portions of the Golden Board image. To define the fiducials, the administrator can use the mouse 98 to select the fiducial button 280 on the tool bar menu 250 of the main window 240, as shown in FIG. 11. The "Fiducials" menu on the menu bar 248 of the main window 240 can also be used. When the fiducial definition function is activated the view frame 270 appears as a small rectangle in the overview window 242, and the corresponding area within the view frame 270 is displayed as a zoomed-in image in the primary window 240. This zoomed-in image shows a corner of a single mask-bounded portion of the Golden Board image as a suggested area for fiducial definition. Zooming in facilitates the precision definition of the fiducial. Additionally, the mouse pointer, which is normally a small arrow, becomes a fiducial definition target 282 formed by a series of concentric rings. When defining the fiducial, the administrator preferably selects an identifiable Golden Board landmark, such as a tooling hole. If the administrator finds no such landmark at the zoomed-in area suggested by the administrative software module, a different area may be selected. To facilitate rapid movement over the Golden Board image, the view frame 270 can be moved by simply clicking the pointer of the mouse 98 anywhere within the overview window 242. This will cause the view frame 270 to be centered on the selected point, and the corresponding zoomed-in image to be displayed in the primary window 240.

Figure 12:
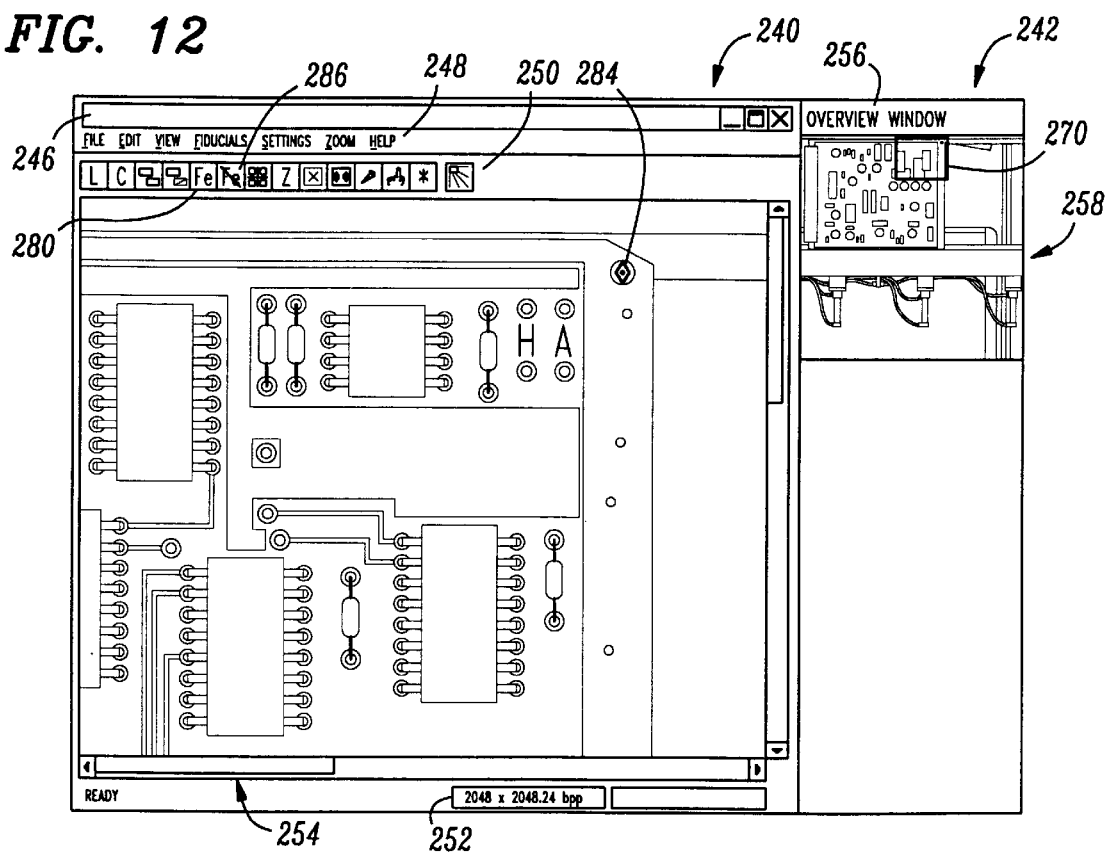
FIG. 12 is a screen-shot view showing a graphical user interface provided during an administrative session of the vision comparison inspection system of FIG. 1, in which a first zoomed area of a known good printed circuit assembly image and a first fiducial mark placed therein are displayed in a primary window and a corresponding thumbnail of the entire known good printed circuit assembly image and a superimposed rectangular view frame are shown in an overview window.

As indicated, the fiducials are preferably defined on significant landmarks, such as tooling holes, and should be as far apart from each other as possible. In FIG. 11, the target 282 is placed over a tooling hole in the upper right-hand corner of a mask-bounded portion of the Golden Board image. The fiducial is set (i.e., its coordinate location is recorded) by clicking the left button of the mouse 98. This causes a fiducial mark 284 to appear, as shown in FIG. 12. The fiducial mark 284 (and its associated fiducial definition) can be deleted by pointing to it with the mouse 98 and pressing the right mouse button. Alternatively, the Delete Fiducial button 286 can be selected on the tool bar 150 of the primary window 240 to delete all fiducial marks (and associated fiducial definitions). The "Fiducials" menu on the menu bar 248 in the main window 240 can also be used.

Figure 13:
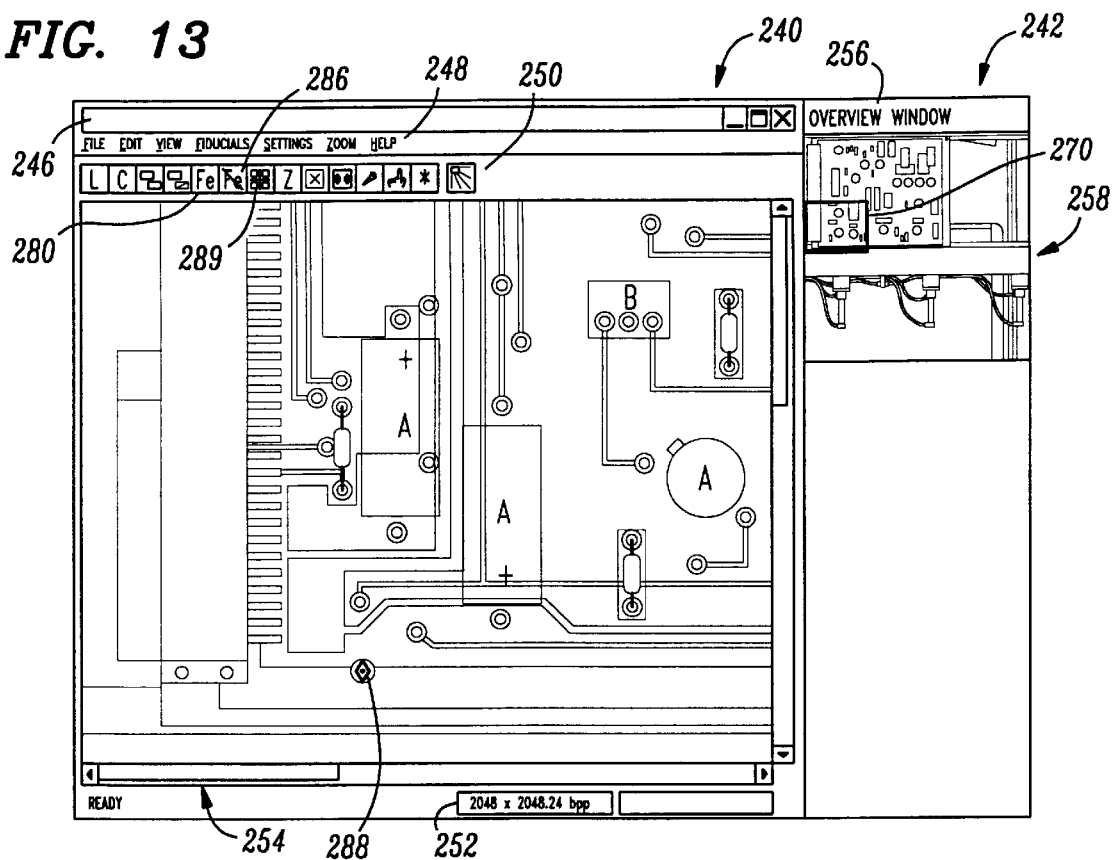
FIG. 13 is a screen-shot view showing a graphical user interface provided during an administrative session of the vision comparison inspection system of FIG. 1, in which a second zoomed area of a known good printed circuit assembly image and a second fiducial mark placed therein are displayed in a primary window and a corresponding thumbnail of the entire known good printed circuit assembly image and a superimposed rectangular view frame are shown in an overview window.

Turning now to FIG. 13, the fiducial definition process is repeated and a second fiducial mark 288 is placed over a tooling hole located an the opposite corner of the same mask-bounded portion of the Golden Board image. It will be seen that the view frame 270 in the overview window 242 is now positioned over the second fiducial location. As indicated, if there are multiple boards such as palletized or panelized boards captured within a single Golden Board image, two fiducials can be defined for each mask-bounded portion of the Golden Board image.

Once the masks and fiducials are defined, the layout can be confirmed by selecting the Confirm Layout button 289 on the tool bar 250 of the main window 240. The "Edit" menu on the menu bar 248 of the main window 240 can also be used. The Golden Board image and the associated mask and fiducial definitions are then stored in on the imaging computer 90's disk drive 231 to provide a reference for all future circuit assemblies of the same type as the Golden Board. An appropriate user-selected filename is assigned to each Golden Board. Invisible to the administrator or the user, the Golden Board image and parameter information is saved in two parts. A graphics file of appropriate size, e.g., twelve megabytes, is created using a conventional graphics format such as TIF, JPEG, GIF or the like to hold the raw Golden Board image. By way of example, this file is stored as FILENAME.TIF, assuming a TIF format is used. A second file, stored as FILENAME.VCD, holds the mask and fiducial coordinate information along with other operational details such as special notes. For ease of use, the administrator and user are only shown the *.VCD files in the "File" menu on the menu bar 248 of the main window 240. They do not normally see the *.TIFF files.

Once the Golden Board files are saved, the administrator software module can be exited. Alternatively, if the administrator wishes to repeat the mask and fiducial definition procedure, the "Edit" menu on the menu bar 248 of the main window 240 allows the administrator to reset the VCD file to delete all mask and fiducial marks.

During production line operations, the user software module 236 is invoked in the imaging computer 90 and usually left running on the screen for use by successive production line shift personnel. Whenever a particular printed circuit assembly type is being setup on the production line 3, the user opens the Golden Board file for that printed circuit assembly by selecting from the File menu in the menu bar 248 of the primary window 240. The user software responds by displaying the Golden Board image on the screen for visual verification that the correct Golden Board has been selected.

As production line operations commence, Test Boards are successively presented to the inspection system 2. Each time a Test Board arrives at the image capture location within the image capture station 40, and a signal on the control cable 150 is provided from the controller 80 to the imaging computer 90 (see FIG. 4), the imaging computer 90 sends a signal to the digital camera 60 on the control and data cable 180 (see FIG. 4) to capture a Test Board image and send it to the imaging computer 90 for processing. The Test Board image is then displayed on the video monitor 92 and the user is prompted with an on-screen message (not shown) to verify whether the image capture was successful. Once the user acknowledges a successful capture, the imaging computer 90 notifies the controller 80 via the control cable 150 to release the Test Board and start the image capture station conveyor 50. The imaging computer 90 simultaneously signals the inspection station 42 via the control cable 222 to start its conveyor 56 in order to receive the Test Board. The Test Board then proceeds to the inspection station 42 and stops in front of the user. As previously described, the video monitor 92, the keyboard 96 and mouse 98 are also in front of the user, as shown in FIG. 1.

Figure 14:
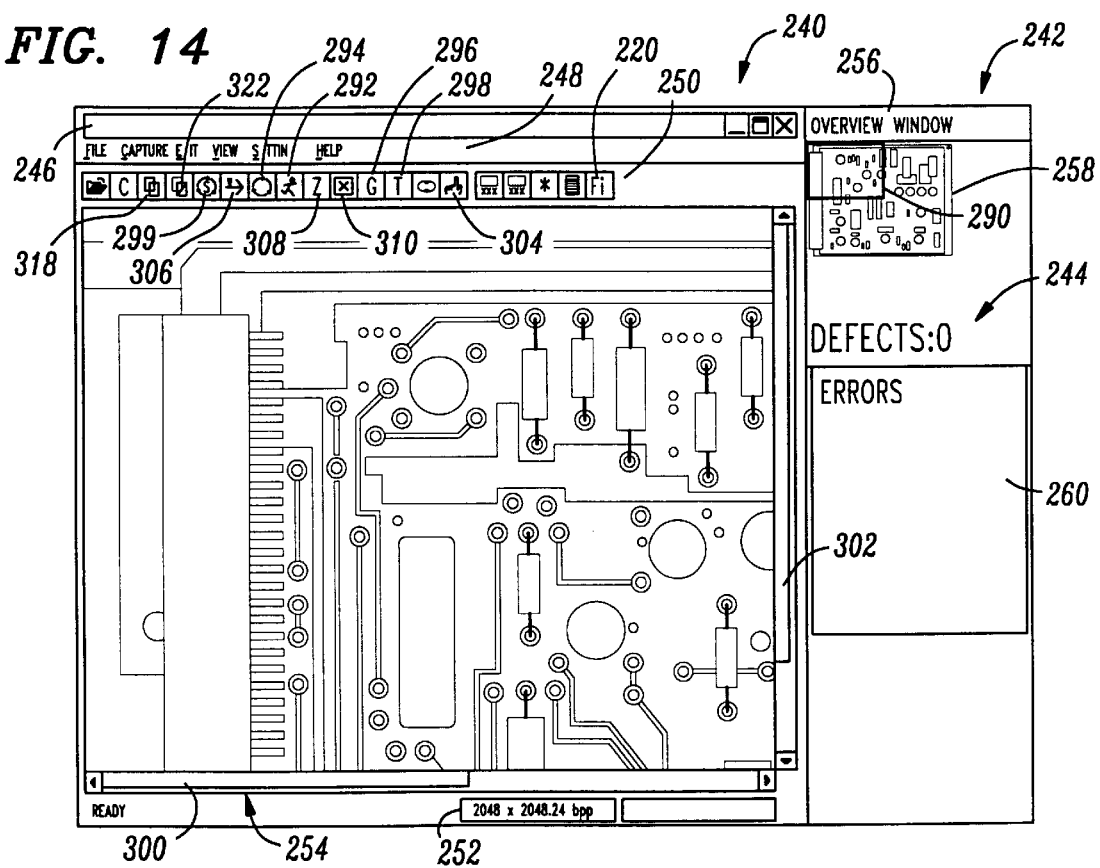
FIG. 14 is a screen-shot view showing a graphical user interface provided during a user session of the vision comparison inspection system of FIG. 1, in which (1) an image of the top left subportion of a mask-bounded portion of a test printed circuit assembly image is displayed in a primary window, (2) a corresponding thumbnail of the entire mask-bounded portion of the test printed circuit assembly image and a superimposed rectangular view frame are shown in an overview window, and (3) an empty defect list window is also shown.

The Test Board image is displayed on the video monitor 92 after the user accepts the captured image. Alternatively, instead of capturing a Test Board image, the user may opt to load a Test Board image from the disk drive 231. In either case, as shown in FIG. 14, the Test Board image is clipped using the mask defined in connection with the Golden Board and a mask-bounded portion of the Test Board image is displayed in the overview window 242. A rectangular view frame 290 is superimposed over the image displayed in the overview window 242 and corresponds to the image that is displayed in the primary window 254. This image represents a subportion of the mask-bounded portion of the Test Board image shown in the overview window 242. As described in more detail below, the subportions of each mask-bounded portion of the Test Board are imaged relative to the corresponding subportions of the Golden Board in a "standard viewing sequence" under the control of the user software module 236.

At this point, both the Golden Board and Test Board images are loaded in the computer 90's memory 232 (preferably in the computer's video buffer). Following alignment enablement (described in more detail below), animation between the corresponding subportions of the two images will be started automatically if an "Auto Run Standard Sequence" selection (not shown) is activated in the "Settings" menu on the menu bar 248 of the main window 240. If Auto Run Standard Sequence is not selected, the standard sequence can be manually commenced by selecting the Standard Sequence button 299 on the tool bar 250 of the main window 240. The user then begins the Golden Board/Test Board comparison process. Preferably, the time delay from the moment a Test Board is imaged by the digital camera 60 to the beginning of animation does not exceed about ten seconds in the automatic mode where Auto Run Standard Sequence is selected.

During animation, a single subportion of the Golden Board and a corresponding single subportion of the Test Board, as delineated by the view frame 290 of the overview window 242, are alternatingly displayed in the primary window 254. This animation presents the Golden Board subportion and the corresponding Test Board subportion for vision comparison inspection. The subportions are displayed at a fifty percent duty cycle at rates varying from as low as one alteration per second to as high as twenty alternations per second. The animation speed can be set by selecting the Animation Speed button 292 in the tool bar 250 of the main window 240. The "Settings" menu in the menu bar 248 of the main window 240 can also be used. As each Golden Board and Test Board subportion is displayed in the primary window 254, a corresponding view of the entire Golden Board or Test Board image, as the case may be, is synchronously displayed in the overview window 242. Although, this overview image may assist the user during automated animation, it is particularly useful during manual animation, described below, in which a user can "single step" between the Golden Board and Test Board images. As each image is selected, the view in the overview window 242 will always correspond to the view in the primary window 254.

The animation preferably continues until the user clicks the left mouse button in the primary window 254, or until the "A" key on the keyboard 96 is pressed (which toggles the animation on and off). The animation can also be stopped and started using the Animation Start/Stop button 294 in the tool bar 250 of the main window 240. After the animation has stopped, the user can toggle manually between the Golden Board and the Test Board subportions by clicking the left mouse button while the mouse pointer is located in the primary window 240. Alternatively, the user can select between the "G" button 296 and the "T" button 298 in the tool bar 250 of the primary window 240 to display the Golden Board and the Test Board (the "Test" board), respectively. Furthermore, the "G" and "T" keys on the keyboard 96 can be used. This allows users to single step between the Golden Board and Test Board images.

Assuming the Test Board was located at the same relative position inside the field of view of the digital camera 60 as the Golden Board was when its image was captured, the displayed subportions of both boards will be positioned at the same location in the primary window 254 as the images are alternatingly displayed. In this ideal situation where the Test Board is aligned with the Golden Board, the flashing images will be congruent. As the two aligned Boards are displayed back and forth, any differences between the two are highlighted because they flash visibly at the animation rate. Realizing that the Golden Board was a "perfect board," if the Test Board has a missing component it will appear only during the Golden Board interval as the two images are alternated. A reversed component will appear to flip its direction 180 degrees back and forth. Wrong components will flash due to the differences between their two images. This comparison thus rapidly highlights differences between the two boards and enables the user to quickly identify defects.

The user software module 236 is programed so that the view frame 290, as shown in FIG. 14, starts in the upper left hand corner of a single mask-bounded portion of the Test Board and Golden Board images, respectively. The view frame 290 is provided to avoid the information overload that might occur if the entire Test Board was inspected in a single view. Each view frame view presents a subportion of the Test Board and corresponding Golden Board and has a size, for example, of 800×600 pixels.

The user software module 236 is programmed to successively move the view frame 290 through the previously-mentioned standard viewing sequence, beginning in the upper left hand corner and finishing at the bottom right hand corner of each mask-bounded portion of the Test Board and Golden Board images. Each subportion view thus shown remains on-screen until the user has completed vision comparison inspection of that view. When the user finishes checking the current subportion view, the next subportion is displayed by pressing the "Enter" key on the keyboard 96. This process is repeated until all the image subportions bounded by a single mask have been visited at least once by the user. Alternatively, left clicking on the Next View button 306 on the tool bar 250 of the main window 240 performs the same function. If multiple masks have been defined on a single Golden Board image, the standard sequence is performed on each mask-bounded portion of the Test Board and Golden Board images.

Once it has commenced, the standard viewing sequence cannot be restarted until a new Test Board image is captured. However, it can be interrupted if the user needs to zoom-in on a component, pan around or scroll the Test Board image, and then return to the current view to continue the viewing sequence. To move freely around the Test Board image, the user can press the left mouse button with the mouse pointer located in the overview window 242. Alternatively, the user can drag the horizontal and vertical scroll bars 300 and 302, respectively, in the primary window 254. Another option is to select the Hand button 304 in the tool bar 250 of the main window 240. This changes the mouse pointer to the shape of a hand. The image in the primary window 254 can then be moved by placing the hand image at some location in the image, pushing the left mouse button to "grab" the image, and then dragging the image in the X-Y direction.

To zoom-in on a portion of the Test Board image, the user can press the letter "Z" on the keyboard 96. Pressing the letter "C" on the keyboard 96 has the opposite effect, i.e., the image is zoomed out. Depressing the "X" key on the keyboard 96 restores the image to original size but the view will not be at the location it was at before zooming was initiated. Pressing the "Enter" key on the keyboard 96 or the Next View button 306 in the tool bar 150 of the main window 250 does restore both the original image size and the current view. Advantageously, this current view is of the most recent standard sequence subportion that was viewed prior to image manipulation, and not of the next subportion of the standard sequence. Zooming can further be performed by selecting the "Z" button 308 in the tool bar 150 of the main window 240. Selecting the "Z" button a second time will end the zoom mode. Selecting the "X" button 310 in the tool bar 150 of the main window 240 will end the zoom mode and return the image to its original size. During the zoom mode, the mouse pointer becomes a magnifying glass. Clicking the left and right mouse buttons is interpreted by the software as a zoom-in and a zoom-out command, respectively.

In some cases, the Test Boards may not always be located at exactly the same location under the digital camera 60 as their counterpart Golden Board was in when its image was acquired. In one exemplary scenario, the printed circuit assemblies might be carried in pallets, as discussed above. It is expected that the positioning of a palletized Test Board under the digital camera 60 might be out of alignment (with respect to a corresponding palletized Golden Board) in X and Y directions and could be rotated as much as five degrees.

For these cases, the user software module 236 optionally provides the ability to align the two images before comparison is made using the fiducial marks defined with respect to the Golden Board by the administrator. More specifically, each mask-bounded portion of a Test Board image can be aligned with each corresponding mask-bounded portion of the Golden Board image. During this "user-assisted" alignment, user intervention with the mouse 98 is used. The software, however, makes this function easy so that no special skill is required on the part of the user.

Within the "Settings" menu on the menu bar 248 of the main window 240, there is a menu selection "Auto Run Align" (not shown). There is also an Align button 318 in the tool bar 250 of the main window 240. Selection of Auto Run Align or the Align button 318 places the system in an operational mode wherein, among other things, a fiducial placement function can be invoked. The Auto Run Align selection places the system in this alignment enablement mode automatically following capture of a Test Board image. The Align button 318 allows the alignment enablement mode to be selected manually. In the preferred embodiment, invocation of the alignment enablement mode by selecting either Auto Run Align or the Align button 318 also enables the standard sequence to be commenced (either automatically by selecting Auto Run Standard Sequence or manually by selecting the Standard Sequence button 299).

As shown in FIG. 14, when Auto Run Align is selected, the Align button 318 is automatically "pushed." If Auto Run Align is not selected, the Align button 318 is not automatically pushed, but can be manually selected by the user. In either case, the system is enabled for alignment but no actual alignment of a Test Board image will occur unless the user further invokes the fiducial placement mode by left clicking the Fi button 320 on the tool bar 250 of the main window 240. Alternatively, the user can invoke the fiducial placement mode using the "Settings" menu in the menu bar 248 of the main window 240.

In either case, if the fiducial placement mode was activated prior to image capture, then following image capture the user will be prompted to place fiducials in the current Test Board image (provided Auto Run Align has been selected or the user pushes the Align button 318). If the fiducial placement mode is selected after image capture, the user needs to then select the Realign button 322 in the tool bar 250 of the main window 240 in order to align the previously unaligned current Test Board image. The Realign button 322 can also be used to realign a previously aligned current Test Board image if the previous alignment was not satisfactory. The Realign button 322 can also be used to restore an aligned current Test Board image to its original unaligned state.

Selecting the Realign button 322 produces a dialog box (not shown) that offers the user a choice of three options, namely, "ReAlign," "No-Align" and "Cancel." The ReAlign option allows the current Test Board image to be aligned if it was not previously aligned, and realigned if it was previously aligned. The No-Align option allows a previously aligned Test Board image to be restored to its unaligned state. The Cancel option simply cancels the user's selection of the Realign button 322. When either the Align or No-Align options are selected, the standard viewing sequence is recommenced and all previously entered defect data (as described below) is deleted.

Figure 15:
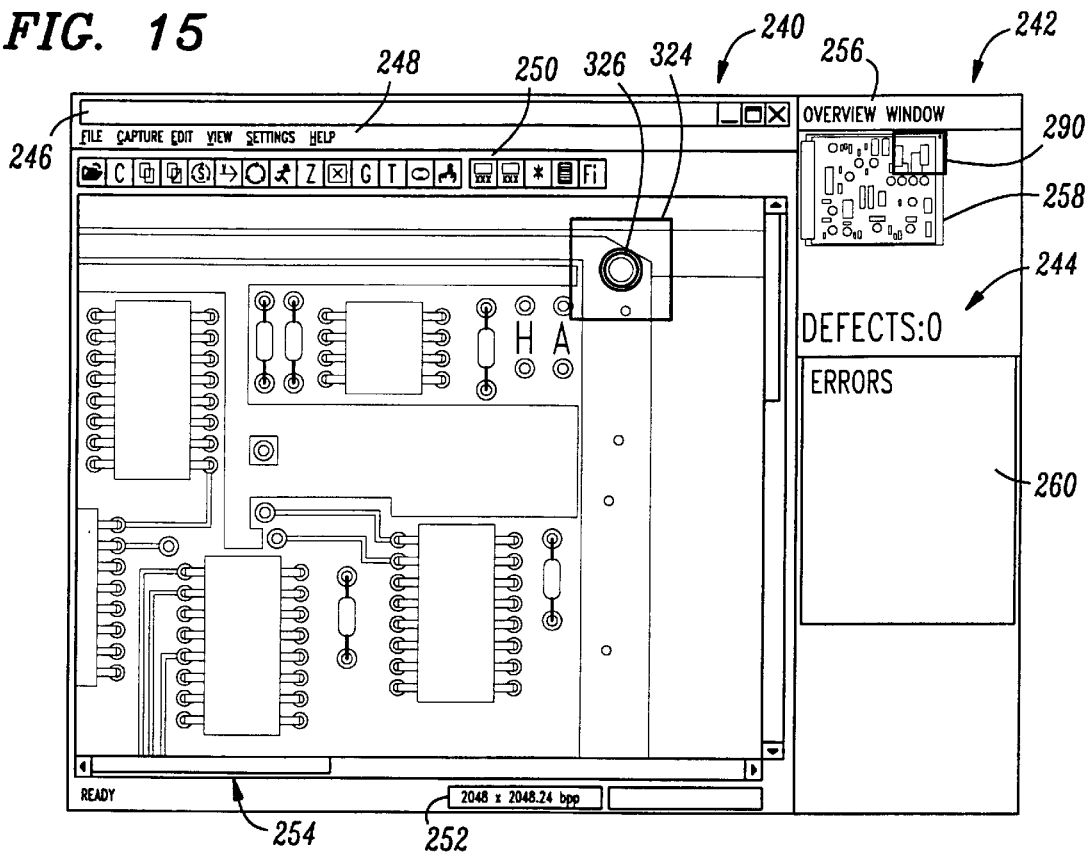
FIG. 15 is a screen-shot view showing a graphical user interface provided during a user session of the vision comparison inspection system of FIG. 1, in which (1) a zoomed area of a mask-bounded portion of a test printed circuit assembly image and a target for placing a first fiducial therein are displayed in a primary window, (2) a corresponding thumbnail of the entire mask-bounded portion of the test printed circuit assembly image and a superimposed rectangular view frame are shown in an overview window, and (3) an empty defect list window is also shown.
Figure 16:
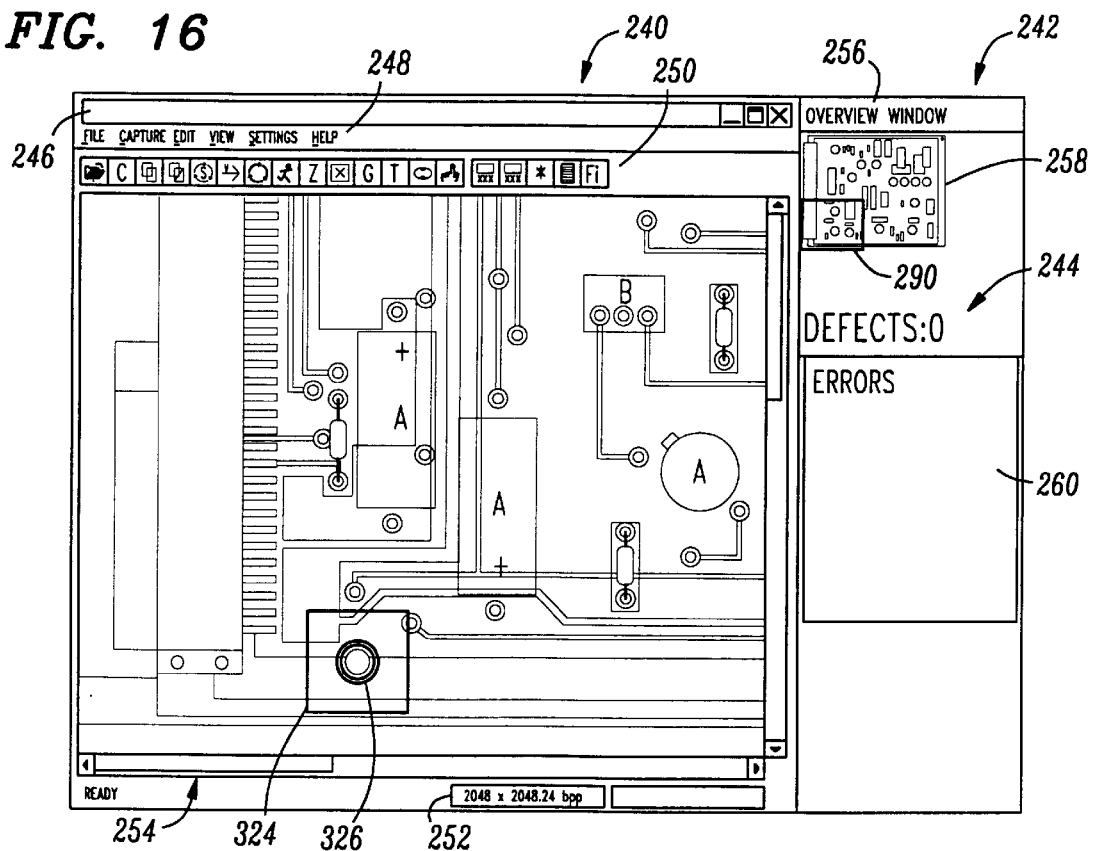
FIG. 16 is a screen-shot view showing a graphical user interface provided during a user session of the vision comparison inspection system of FIG. 1, in which (1) a zoomed area of a mask-bounded portion of a test printed circuit assembly image and a target for placing a second fiducial therein are displayed in a primary window, (2) a corresponding thumbnail of the entire mask-bounded portion of the test printed circuit assembly image and a superimposed rectangular view frame are shown in an overview window, and (3) an empty defect list window is also shown.

Turning now to FIG. 15, during fiducial placement operations, the user software module 236 prompts the user to place a pair of fiducials in each mask-bounded portion of the Test Board, and these fiducials are used to align the mask-bounded portion(s) of the Test Board image with the corresponding mask-bounded portion(s) of the Golden Board image. The fiducial mark placement process is analogous to the fiducial definition procedure performed during the administrative mode. When the fiducial mark placement process begins, the user control module software determines the coordinates of the Golden Board fiducials for one mask-bounded portion thereof. The system then displays, in the primary window 254, an area of the mask-bounded portion of the Test Board image representing the approximate location of the first of such Golden Board fiducials, and also zooms the image. A small fiducial placement box 324 is also displayed in the primary window 254 centered on the coordinates of the first Golden Board fiducial. At the same time, the mouse pointer becomes a target image 326. In most cases, the fiducial placement box 324 will enable the user to locate the correct location for placement of the Test Board fiducial. If there is any doubt, the user can consult the Golden Board image to verify where its fiducial is defined and then place a corresponding fiducial in the Test Board image. Once the first Test Board fiducial is placed, the user control module 236 displays an area of the mask-bounded Test Board image representing the approximate location of the second Golden Board fiducial, while still in the zoom mode, and displays the fiducial placement box 324, as shown in FIG. 16. The user then uses the mouse target pointer 326 to place the second Test Board fiducial. Once both fiducials are placed in a mask-bounded portion of the Test Board image, the system aligns the mask-bounded portion of the Test Board image with the corresponding mask-bounded portion of the Golden Board image. The image comparison inspection process, i.e., the standard sequence, then commences on the aligned mask-bounded portion of the Test Board image.

Figure 17:
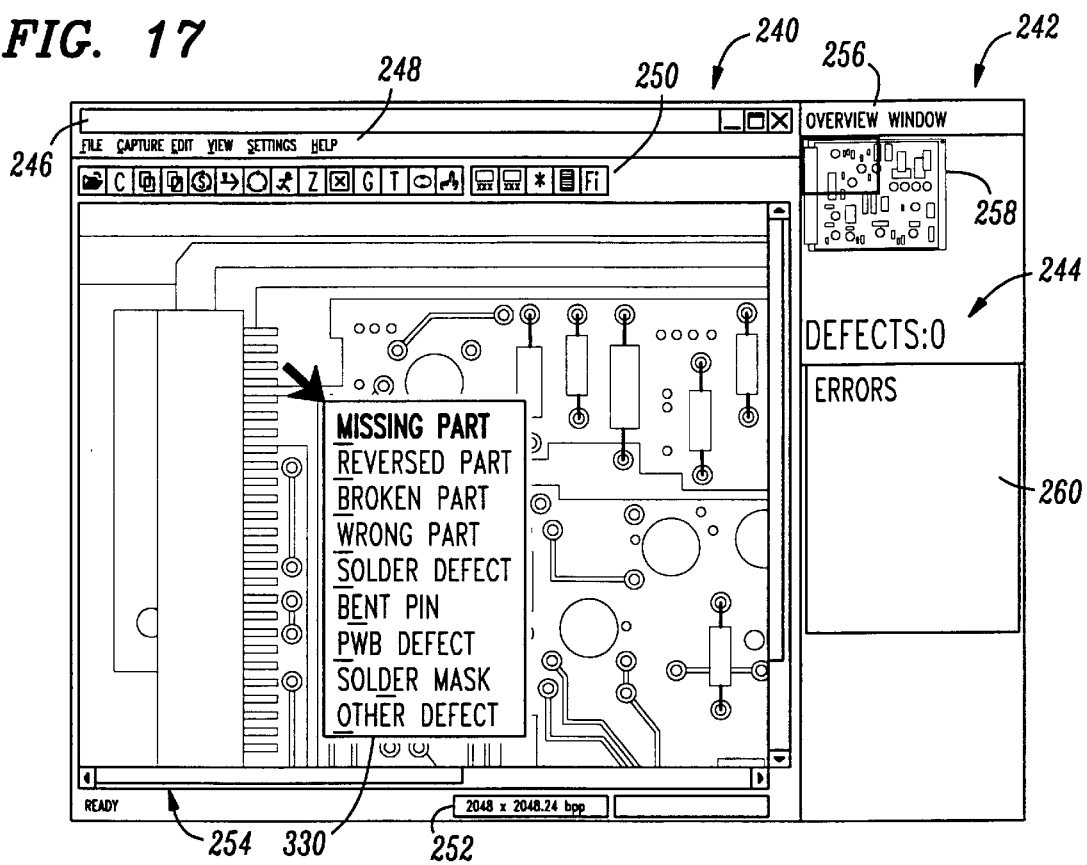
FIG. 17 is a screen-shot view showing a graphical user interface provided during a user session of the vision comparison inspection system of FIG. 1, in which (1) a top left subportion of a mask-bounded portion of a test printed circuit assembly image and a pop-up defect list menu are displayed in a primary window, (2) a corresponding thumbnail of the entire mask-bounded portion of the test printed circuit assembly image and a superimposed rectangular view frame are shown in an overview window, and (3) an empty defect list window is also shown.

At any time during the comparison inspection process, the user can input standard defect data for collection in a database. This database can be used as a valuable information tool to identify defect patterns that arise during the production process. Defects are noted by tagging the Test Board image. FIG. 17 shows an example of a defect and the action to be taken by a user to tag the defect. The defect is assumed to be a missing part. The operator moves the mouse pointer to the center of the defect area and presses the right mouse button. This displays a defect menu 330 that lists possible defects. A separate spawned menu could also be used to provide a defect source menu that allows the operator to specify the source of the defect (i.e., the production line location where the defect was introduced).

Figure 18:
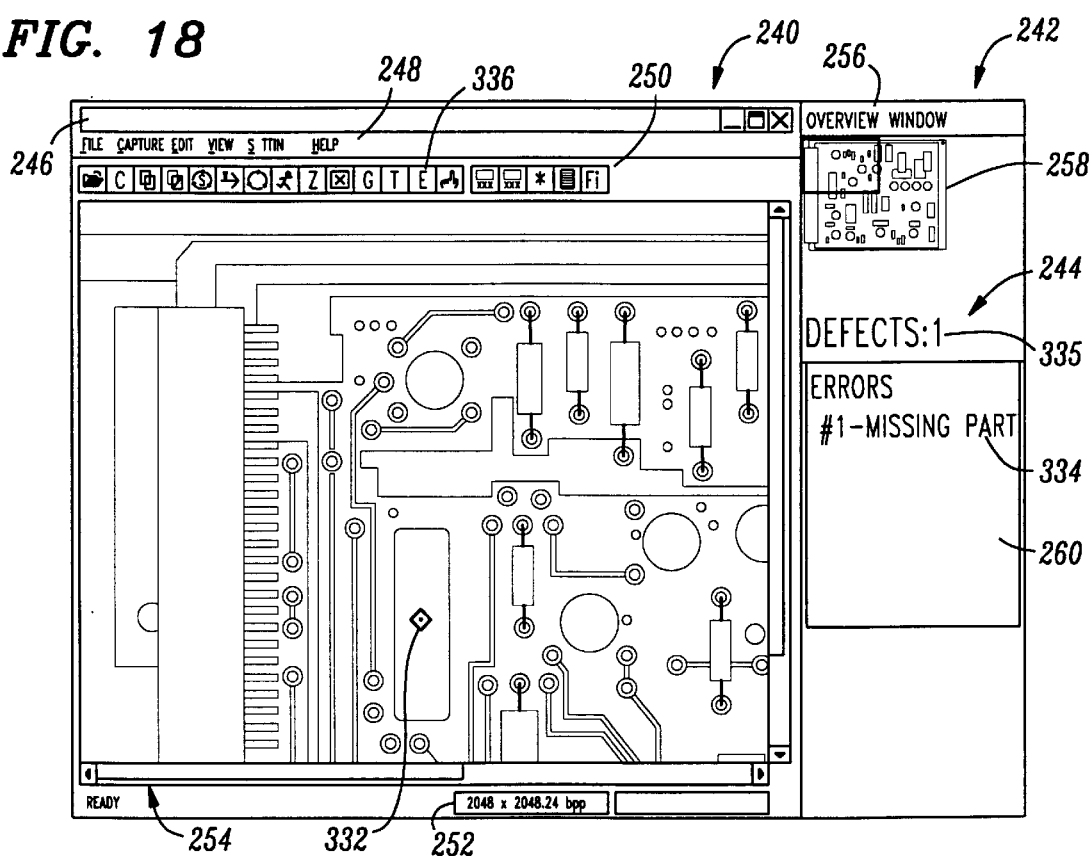
FIG. 18 is a screen-shot view showing a graphical user interface provided during a user session of the vision comparison inspection system of FIG. 1, in which (1) a top left subportion of a mask-bounded portion of a test printed circuit assembly image and a tagged defect are displayed in a primary window, (2) a corresponding thumbnail of the entire mask-bounded portion of the test printed circuit assembly image with the same tagged defect and a superimposed rectangular view frame are shown in an overview window, and (3) a defect identified in the test printed circuit assembly is shown in a defect list window.

In the example of FIG. 17, the operator moves the mouse pointer inside the defect menu 330 and left-clicks the "Missing Part" selection. As shown in FIG. 18, this causes the defect menu 330 to disappear and a small yellow diamond 332 to appear at the defect position in the image. At the same time, a corresponding entry 334 is added to the defect list box 260. The defect list box 260 keeps a record of all the defects that are marked in the Test Board image. When the first defect is entered, a Defect button 336 in the tool bar 250 of the main window 240 displays the letter "F" for "Error" and assumes a "pressed" position.

Figure 19:
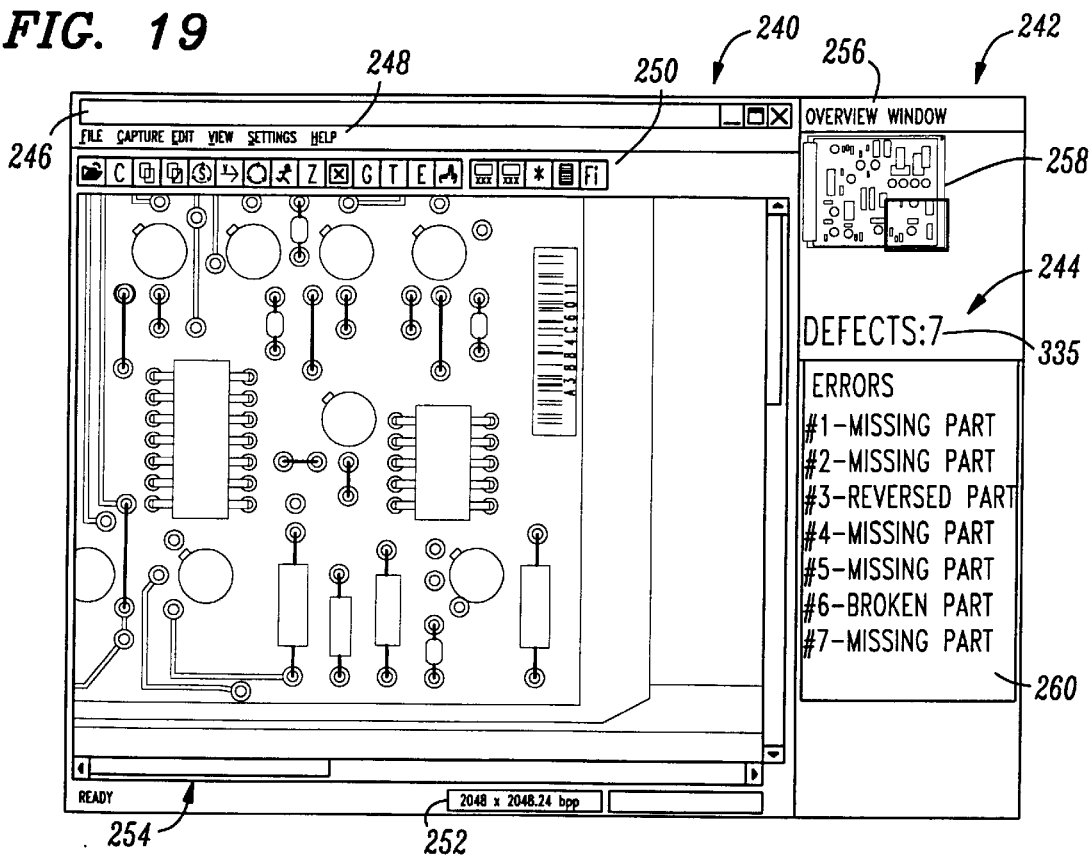
FIG. 19 is a screen-shot view showing a graphical user interface provided during a user session of the vision comparison inspection system of FIG. 1, in which (1) a bottom right subportion of a mask-bounded portion of a test printed circuit assembly image is displayed in a primary window, (2) a corresponding thumbnail of the entire mask-bounded portion of the test printed circuit assembly image and a superimposed rectangular view frame are shown in an overview window, and (3) a list of defects identified in the test printed circuit assembly is shown in a defect list window.

In FIG. 18, the defect list box 260 indicates that one defect has been marked and is a "missing part" defect. After the first view of the Test Board is marked, the user can cycle to the subsequent views and mark defects found therein, until the last view is reached, as shown in FIG. 19. The defect list box 260 now lists seven defects and identifies their nature. A defect count indicator 335 is also shown above the defect list box 260. Each defect is marked with a yellow diamond in the views displayed in the primary window 254. Additionally, the defects are displayed in the overview window 242 as red diamonds (not shown). This provides the operator a total view of all of the marked defects even though only one view of the Test Board is visible at one time in the primary window 254. By clicking on a red diamond in the overview window 242, the view frame 290 moves and the image in the primary window 254 shifts to the location of the selected diamond. Optionally, the operator can deselect the Defect button 336 to blank out the defect diamonds 322 in the primary window 254. The red diamonds in the overview window 242 are unaffected.

Figure 20:
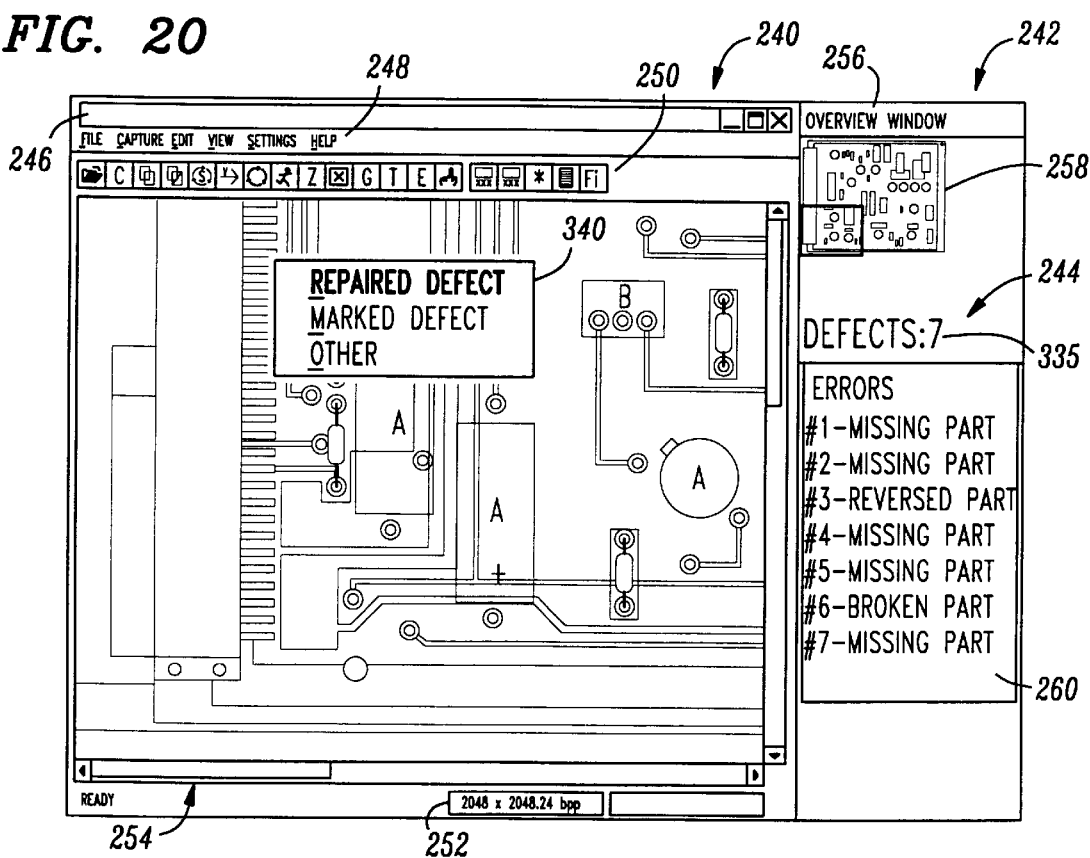
FIG. 20 is a screen-shot view showing a graphical user interface provided during a user session of the vision comparison inspection system of FIG. 1, in which (1) a bottom left subportion of a mask-bounded portion of a test printed circuit assembly image and a pop-up window requesting defect resolution information are displayed in a primary window, (2) a corresponding thumbnail of the entire mask-bounded portion of the test printed circuit assembly image and a superimposed rectangular view frame are shown in an overview window, and (3) a list of defects identified in the test printed circuit assembly is shown in a defect list window.
Figure 21:
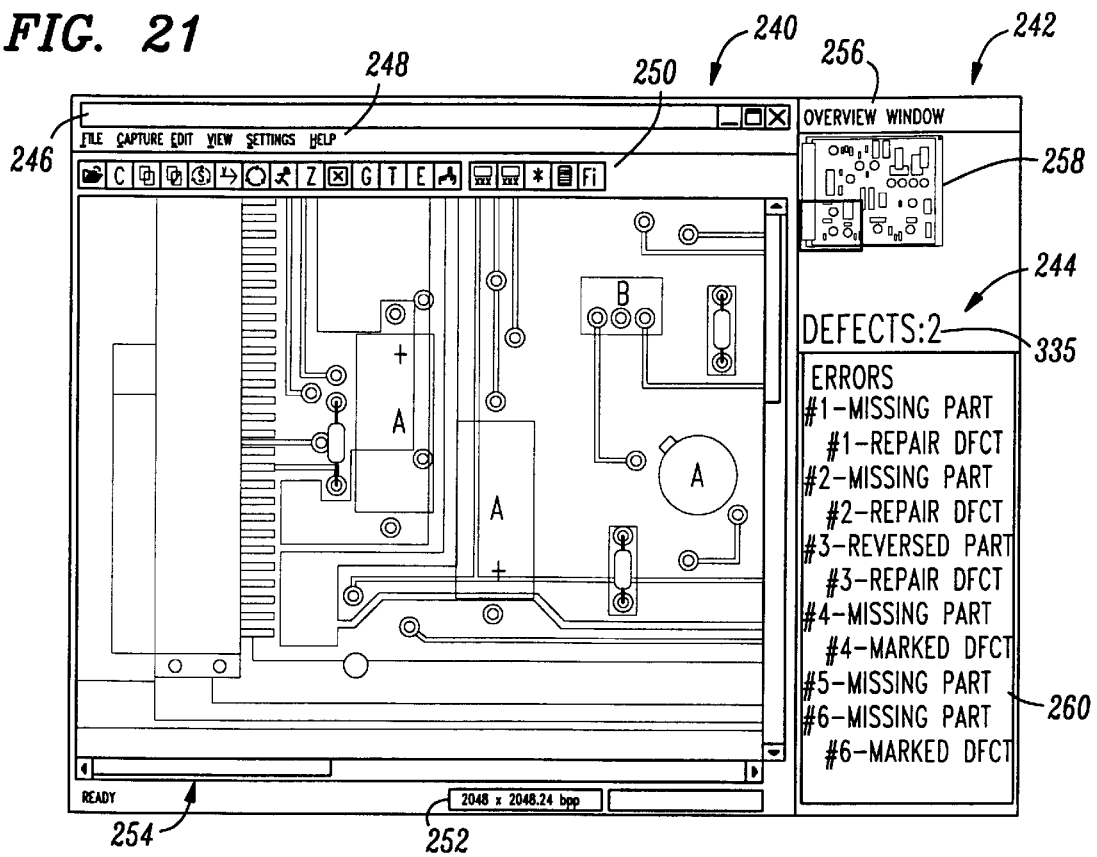
FIG. 21 is a screen-shot view showing a graphical user interface provided during a user session of the vision comparison inspection system of FIG. 1, in which (1) a bottom left subportion of a mask-bounded portion of a test printed circuit assembly image is displayed in a primary window, (2) a corresponding thumbnail of the entire mask-bounded portion of the test printed circuit assembly image and a superimposed rectangular view frame are shown in an overview window, and (3) a list of defects identified in the test printed circuit assembly and the manner in which such defects were resolved are shown in a defect window.

Although all of the defective parts have been marked in FIG. 19, no defect resolution has yet taken place. The defect resolution mode is not entered until the standard viewing sequence has completed. When it does, the user software module 236 displays a message (not shown) reminding the operator that there are one or more defects to be resolved. Thereafter, in order for the Test Board to be released from the inspection system 2, or the next mask-bounded subportion of Test Board image to be inspected, the defects must be resolved, either by fixing the problem or advising the inspection system 2 that the defects will be resolved at some other time. To advise the inspection system 2 following the resolution of a defect, the operator places the mouse pointer over or near the diamond 332 corresponding to the resolved defect in the primary window 254 and presses the left mouse button. A pop-up menu 340 appears, as shown in FIG. 20, and presents a list of possible resolutions. This resolution pop-up menu 340 can only be invoked within a defined vicinity of the defect diamond. As the resolution for each defect is selected, the yellow diamond 332 turns to green. At the same time, the resolution information is added to the defect list box 260 and the defect count indicator 335 is decremented, as shown in FIG. 21. Furthermore, the corresponding red diamond in the overview window 242 disappears.

Figure 22:
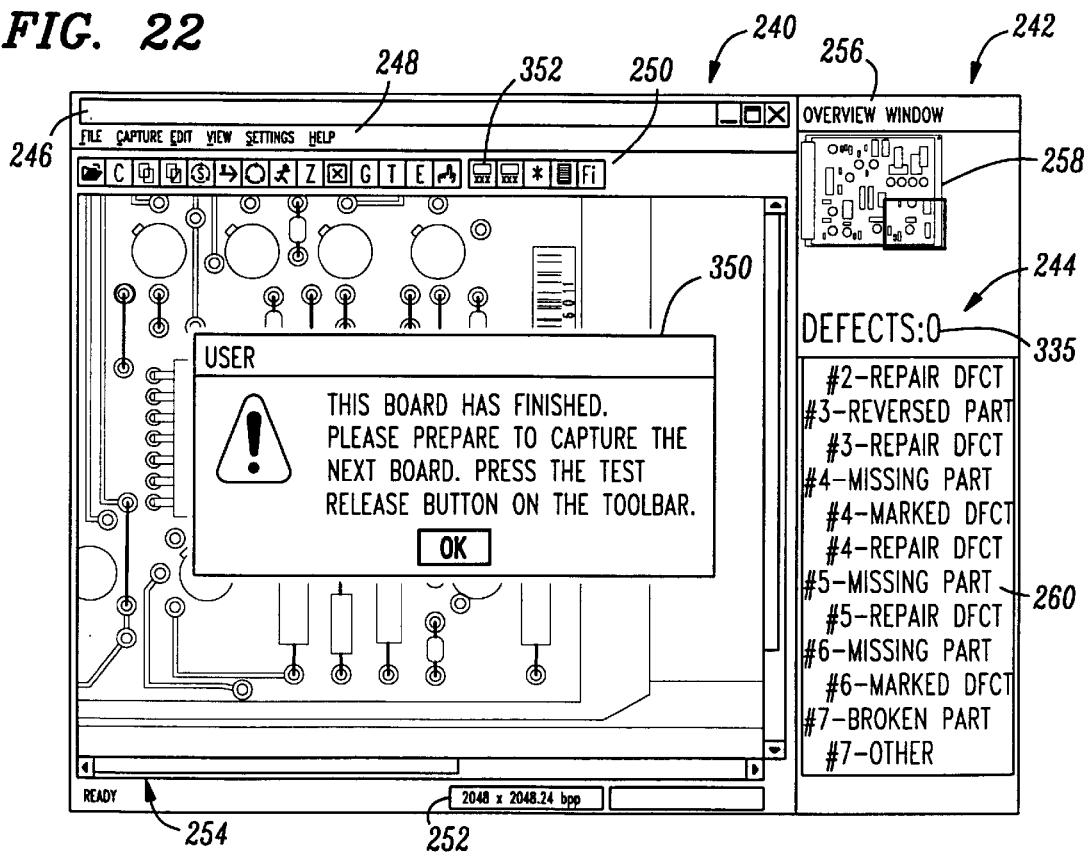
FIG. 22 is a screen-shot view showing a graphical user interface provided during a user session of the vision comparison inspection system of FIG. 1, in which (1) a bottom right subportion of a mask-bounded portion of a test printed circuit assembly image and a pop-up menu advising that the test printed circuit assembly may be released from the inspection station are displayed in a primary window, (2) a corresponding thumbnail of the entire mask-bounded portion of the test printed circuit assembly image and a superimposed rectangular view frame are shown in an overview window, and (3) a fully resolved defect list is also shown.

When all defects are resolved in all mask-bounded portions of the Test Board image, the software displays the dialog box 350 shown in FIG. 22. This dialog box advises that the current Test Board has finished, to prepare for capture of the next Test Board, and to release the current Test Board (by right clicking the Test Board Release button 352 in the tool bar 250 of the main window 240, or pushing the manual board release button mounted on the inspection station control panel 102 (See FIG. 1)).

Figure 23:
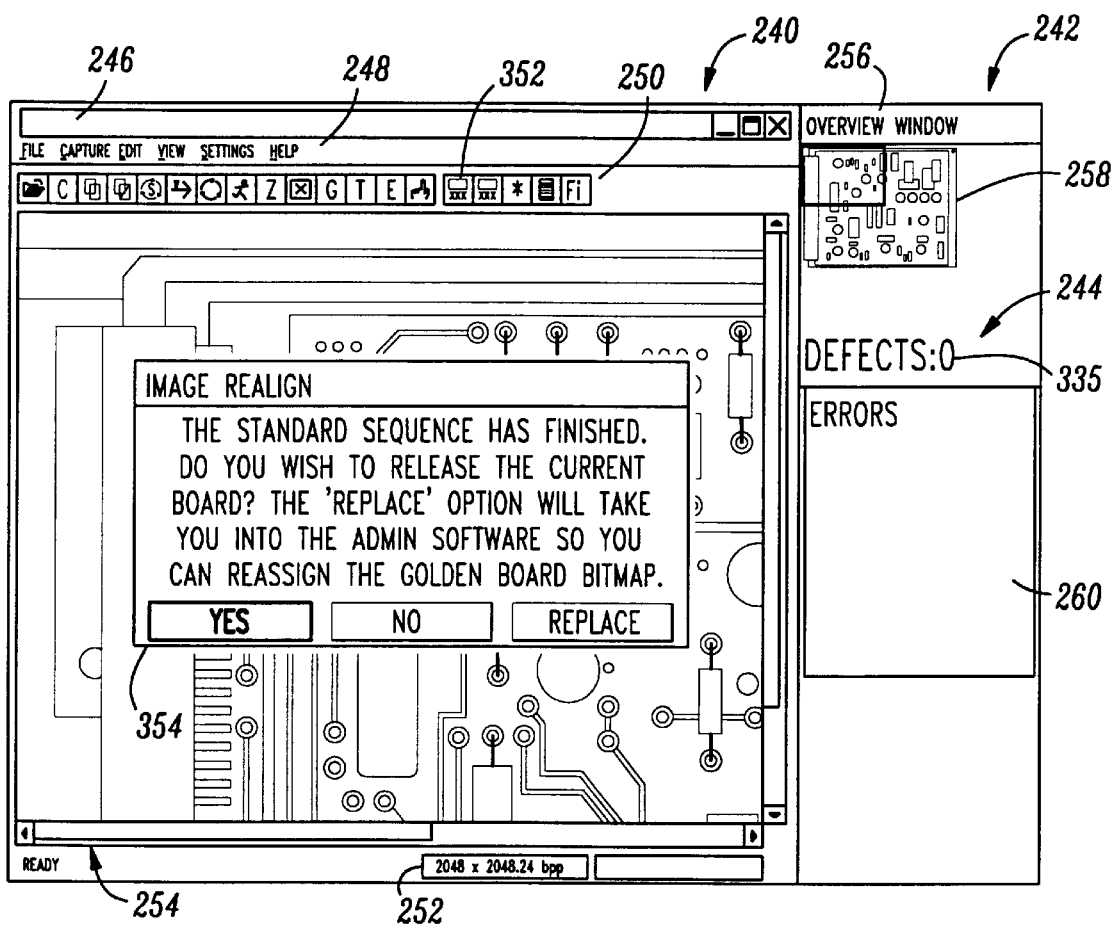
FIG. 23 is a screen-shot view showing a graphical user interface provided during a user session of the vision comparison inspection system of FIG. 1, in which (1) a top left subportion of a mask-bounded portion of a test printed circuit assembly image and a pop-up menu soliciting optional operations reserved for test printed circuit assemblies without defects are displayed in a primary window, (2) a corresponding thumbnail of the entire mask-bounded portion of the test printed circuit assembly image and a superimposed rectangular view frame is shown in an overview window, and (3) an empty defect list window is also shown.

Turning now to FIG. 23, if the Test Board has no defects, which is normally the case, a dialog box 354 is displayed, which allows the operator three options. First, the operator can release the Test Board to proceed to the wave solder machine. Second, as in the case of a defective Test Board, the operator can retain the Test Board for further inspection. The operator can still animate and pan around the Test Board as described above. This may be desired so that the Test Board can be revisited prior to release. In order to release the Test Board, the user must select the Test Board Release button 352 with the mouse pointer or, alternatively, push the manual board release button mounted on the inspection station control panel 102 (see FIG. 1). Unless and until the current Test Board is released from the inspection station 42, no new Test Board will be received by the image capture station 40. A new Test Board will not be allowed into the image capture station 40 until the imaging computer 90 advises the controller 80 that the current Test Board has been released.

The third option in the menu 350 allows the current Test Board to be upgraded to Golden Board as a replacement for the current Golden Board. Establishing upgraded Golden Boards in this way may be desirable from time to time as component substitutions or changes in component labeling are made on the production line. Such changes raise the level of undesirable visual "flash" noise during the inspection process. Promoting Test Board to a Golden Board has the effect of upgrading the Golden Board image to more closely match current production batches.

Selection of the Golden Board replacement option in the menu 350 causes the user software module 236 to close and the administrative software module 234 to open. The old Golden Board image is replaced with that of the current Test Board. Importantly, a new image need not be captured and the previously defined mask and fiducial marks may be reused. In many cases, however, it is advantageous to define a new mask and new fiducial marks. An additional feature of the user software module 236 is that Test Board images may be stored as such in the disk drive 231 for future reference.

Figure 24:
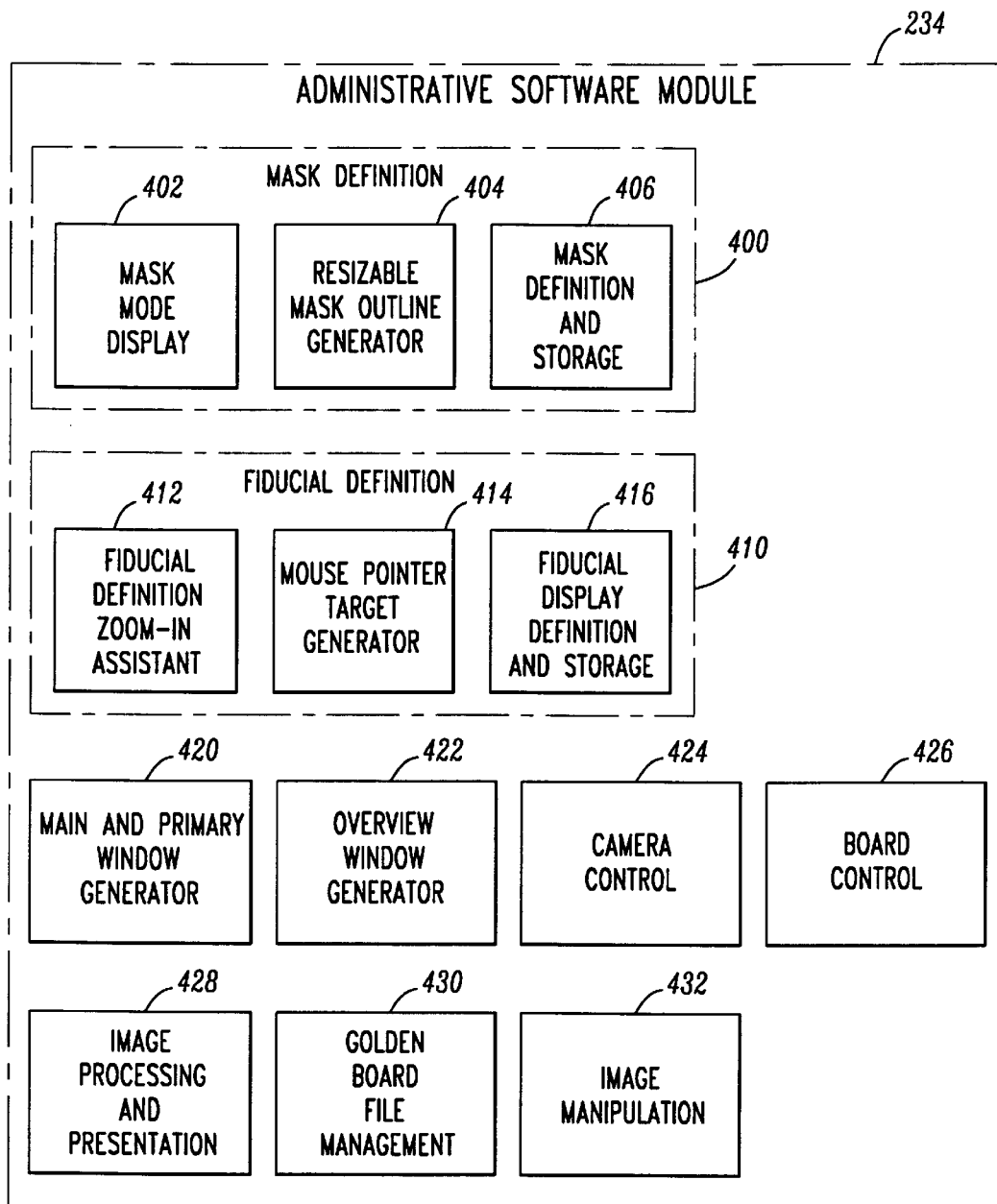
FIG. 24 is a block diagram showing software components of an administrative software module that may be incorporated as part of the vision comparison inspection system of FIG. 1.
Figure 25:
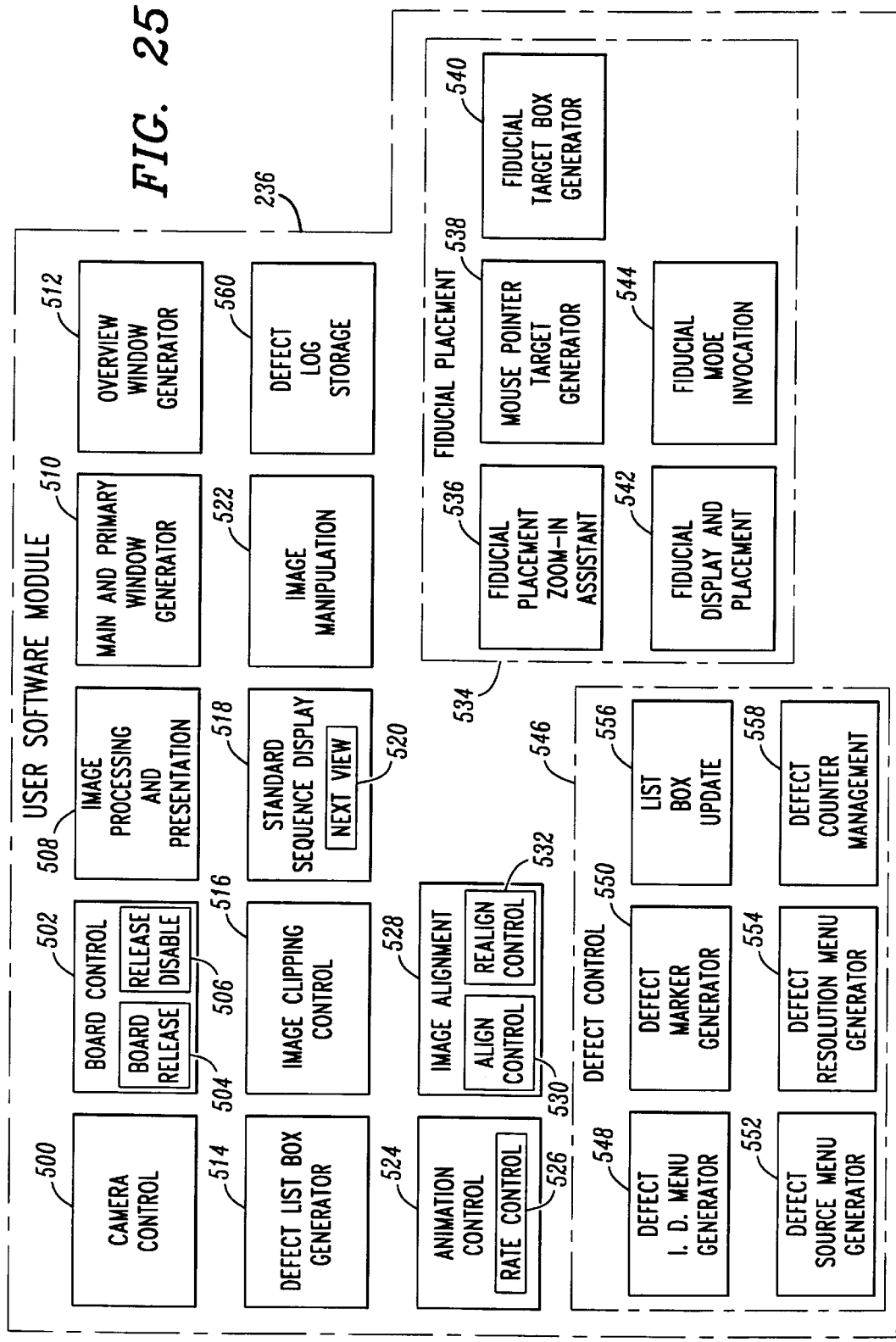
FIG. 25 is a block diagram showing software components of a user software module that may be incorporated as part of the vision comparison inspection system of FIG. 1.

Turning now to FIGS. 24 and 25, the administrative software module 234 and the user software module 236 are illustrated in block diagram form in which all of the previously described functional elements are shown as block diagram components.

FIG. 24 shows the administrative software module as including a mask definition module 400 that comprises a mask mode display component 402 for presenting the entire Golden Board image for mask definition as shown in FIG. 10, a resizable mask outline generator component 404 for generating the resizable mask outline 274 of FIG. 10, and a mask definition component 406 for setting the mask definition and storing it in the Golden Board parameter file.

FIG. 24 further shows that the administrative software module 234 includes a fiducial definition module 410 that comprises a fiducial definition zoom-in assistant component 412 for zooming to a fiducial definition area of the Golden Board as shown in FIGS. 11–13, a mouse pointer target generator component 414 for generating the fiducial target pointer 282 of FIG. 11, and a fiducial display, definition and storage component 416 for displaying the fiducial marks 284 and 288 of FIGS. 11 and 13, and for setting the fiducial definition and storing it in the Golden Board parameter file.

FIG. 24 further shows that the administrative software module 234 includes a main and primary window generator component 420 for generating the main and primary windows 240 and 254 of FIGS. 9–13, along with all of the graphical user interface control elements in the menu bar 248 and the tool bar 250. There is also an overview window generator component 422 for generating the overview window 242 of FIGS. 9–13, along with the viewing rectangle 270 therein. There is a camera control component 424 for signaling the camera 60 to capture an image, and a board control component 426 for controlling the release of Golden Boards from their image capture and inspection positions. An image processing and presentation component 428 is provided for processing captured Golden Board images and displaying them in the overview window 242 and the primary window 254 of FIGS. 9–13, respectively. A Golden Board file management component 430 is provided to create and manage Golden Board files. Lastly, an image manipulation component 432 allows an administrator to zoom, pan and scroll around a Golden Board image in the primary window 254 of FIGS. 9–13.

FIG. 25 shows the user software module as including a camera control component 500 for signaling the camera 60 to capture a Test Board image. A board control component 502 is provided to control the release of Test Boards from their image capture and inspection positions. The board control module 502 includes a board release component 504 for releasing a Test Board from its inspection position and a release disable component 506 to prevent a user from releasing a Test Board from its inspection position. An image processing and presentation component 508 is provided for processing captured Test Board images and displaying them in the overview window 242 and the primary window 254 of FIGS. 14–23, respectively. A main and primary window generator component 510 is provided for generating the main and primary windows 240 and 254 of FIGS. 14–23, along with all of the graphical user interface control elements in the menu bar 248 and the tool bar 250. An overview window generator component 512 generates the overview window 242 of FIGS. 14–23, along with the viewing rectangle 290 therein. A defect list box generator component 514 generates the defect list area 244 and defect list box 260 of FIGS. 14–23.

The user software module 236 further includes an image clipping control component 516 for clipping Test Board image information outside the mask bounded portions thereof A standard sequence display module 518 controls the standard viewing sequence described above. It includes a next view component 520 for stepping through the image subportion views of each standard sequence. An image manipulation component 522 allows users to zoom, pan and scroll around Test Board images. An animation control module 524 generates the Golden Board/Test Board animation in the primary window 254 and the overview window 242 in FIGS. 14–23. It includes an animation rate control component 526 for changing the speed of animation.

The user software module 236 further includes an image alignment module 528 for performing image alignment as described above. This module includes an align control component 530 for implementing the alignment enablement mode and a realign control component for implementing the realign functions described above. A fiducial placement module 534 includes a fiducial placement zoom-in assistant component 536 for zooming to a fiducial placement area of the Golden Board as shown in FIGS. 15 and 16, a mouse pointer target generator component 538 for generating the fiducial target pointer 326 of FIGS. 15 and 16, a fiducial target box generator component 540 for generating the target box 324 of FIGS. 15 and 16, and a fiducial display and placement component 542 for displaying the fiducial marks illustrating the fiducials placed by the user, and for generating the fiducial placement information used for image alignment.

A defect control module 546 includes a defect identification menu generator component 548 for generating the pop-up menu 330 of FIG. 17. There is also a defect marker generator component 550 for generating the defect marker 332 in the primary window 254 of FIG. 18, along with the corresponding defect marker (not shown) in the overview window 242. A defect source menu generator 552 generates the defect source menu described above (not shown). A defect resolution menu generator component 554 generates the pop-up menu 340 of FIG. 20. A defect list box update component 556 generates and maintains the list of defects shown in the defect list box 260 of FIGS. 14–23. A defect counter management component 558 generates and maintains the defect counter 335 of FIGS. 18–23. Lastly, a defect log storage component 560 generates and maintains the defect log file described above.

Accordingly, a vision comparison inspection system has been described. While various embodiments have been disclosed, it should be apparent that many variations and alternative embodiments would be apparent to those skilled in the art in view of the teachings herein. For example, rather than use a digital camera for image capture, a high resolution scanner positioned in close proximity to the image capture station conveyor 50 could be used to capture images of printed circuit assemblies carried thereon. In addition, a flash lamp system could be used in lieu of the flourescent lighting system herein described, although the power requirements for the former would be considerably higher than the latter. It is understood, therefore, that the invention is not to be in any way limited except in accordance with the spirit of the appended claims and their equivalents.

What is claimed is:

1. A vision comparison inspection system for use in association with a printed circuit assembly production line, said vision inspection system comprising:

an electronic image capture device fixedly positioned to capture an image (Test Board image) of the entirety of a printed circuit assembly under test (Test Board);

a lighting system for illuminating said Test Board;

an imaging control system receiving the output of said image capture device and including a programmed image processing computer, an electronic display device and an input device;

an administrative control module in said imaging control system for creating files containing images (Golden Board images) corresponding to known good circuit assemblies (Golden Boards);

a user control module in said imaging control system including image processing means for processing said Test Board image and animation means for alternatingly displaying a Golden Board image and said Test Board image on said display device, whereby defects in said printed circuit assembly under test can be visually identified using said Test Board image without the need to reposition said image capture device or said Test Board; and said administrative control module further comprising an administrative mode graphical user interface including an administrative mode primary window and an administrative mode overview window, said administrative mode overview window displaying said Golden Board image within the field of view of said electronic image capture device and an administrative mode viewing rectangle superimposed over said Golden Board image, and said administrative mode primary window displaying the portion of said Golden Board image located within said administrative mode viewing rectangle.

2. A vision comparison inspection system in accordance with claim 1 wherein said Golden Board and Test Board images include an image of said Golden Board and said Test Board, respectively, together with other information within the field of view of said image capture device, and wherein said administrative control module includes mask means responsive to input from an administrator for defining a mask in said Golden Board image that encompasses the boundaries of said Golden Board, and wherein said user control module includes image clipping means for automatically applying said mask to said Test Board and Golden Board images such that only Test Board and Golden Board image information within said mask is shown when said Test Board and said Golden Board are alternatingly displayed.

3. A vision comparison inspection system in accordance with claim 1 wherein said Golden Board and Test Board images include images of plural palletized or panelized Golden Boards and Test Boards, respectively, together with other information within the field of view of said image capture device, and wherein said administrative control module includes mask means responsive to input from an administrator for defining plural masks in said Golden Board image that delimit the boundaries of each of said palletized or panelized Golden Boards, and wherein said user control module includes image clipping means for automatically applying said masks to said Test Board and Golden Board images such that only Test Board and Golden Board image information within said plural masks is shown when said Test Board and Golden Board images are alternatingly displayed.

4. A vision comparison inspection system in accordance with claim 2 wherein said administrative control module includes administrative mode fiducial definition means responsive to input from an administrator for defining a pair of Golden Board fiducials in the mask-bounded portion of said Golden Board image, and wherein said user control module includes user mode fiducial placement means responsive to input from a user for placing Test Board fiducials in the portion of said Test Board image that is bounded by said mask and for aligning the mask-bounded portion of said Test Board image with the mask-bounded portion of said Golden Board image using said Golden Board fiducials and said Test Board fiducials.

5. A vision comparison inspection system in accordance with claim 3 wherein said administrative control module includes administrative mode fiducial means responsive to input from an administrator for defining a pair of Golden Board fiducials in each mask-bounded portion of said Golden Board image, and wherein said user control module includes user mode fiducial means responsive to input from a user for placing a pair of Test Board fiducials in the portions of said Test Board image bounded by said Golden Board masks, and for aligning the mask-bounded portions of said Test Board image with the corresponding mask-bounded portions of said Golden Board image using said Golden Board fiducials and said Test Board fiducials.

6. A vision comparison inspection system in accordance with claim 1 wherein said user control module includes defect log means responsive to input from a user for generating a log of defects found in said Test Board and storing said defect log in one or more records of a defect log file.

7. A vision comparison inspection system in accordance with claim 6 wherein said defect log specifies for each defect listed therein, a defect type, a defect location on said Test Board, and a defect resolution.

8. A vision comparison inspection system in accordance with claim 7 wherein said defect log further specifies for each defect listed therein a defect source.

9. A vision comparison inspection system in accordance with claim 1 wherein said Golden Board and Test Board images include an image of said Golden Board and said Test Board, respectively, together with other information within the field of view of said image capture device, and wherein said administrative control module further comprises;

mask mode display means responsive to administrator input for displaying all of said Golden Board image in said administrative mode primary window;

mask outline generation means responsive to administrator input for generating an adjustably sizeable mask outline in said administrative mode primary window; and mask definition means responsive to administrator input for defining a mask corresponding to said mask outline that delimits the boundaries of said Golden Board, said mask being for subsequently clipping said Test Board and Golden Board images such that only Test Board and Golden Board image information within said mask is shown when said Test Board and Golden Board images are alternatingly displayed.

10. A vision comparison inspection system in accordance with claim 1 wherein said Golden Board and Test Board images include images of plural palletized or panelized Golden Boards and Test Boards, respectively, together with other information within the field of view of said image capture device, and wherein said administrative control module further comprises;

mask mode display means responsive to administrator input for displaying all of said Golden Board image in said administrative mode primary window;

mask outline generation means responsive to administrator input for generating plural adjustably sizeable mask outlines in said administrative mode primary window; and mask definition means responsive to administrator input for defining plural masks corresponding to said plural mask outlines that delimit the boundaries of said palletized or panelized Golden Boards, said masks being for subsequently clipping said Test Board and Golden Board images such that only Test Board and Golden Board image information within said plural masks is shown when said Test Board and Golden Board images are alternatingly displayed.

11. A vision comparison inspection system in accordance with claim 9 wherein said administrative control module further comprises:

administrative mode fiducial display means responsive to administrator input for displaying in said administrative mode primary window zoomed-in portions of said Golden Board image to assist in defining a pair of Golden Board fiducials at selected Golden Board landmarks within the mask-bounded portion of said Golden Board image;

administrative mode target pointer means for generating a movable target image in said administrative mode primary window that assists in precisely defining the locations of said Golden Board fiducials; and administrative mode fiducial definition means responsive to administrator input for defining said Golden Board fiducials at locations indicated by said target image in said administrative mode primary window, and for generating Golden Board fiducial mark images at said fiducial locations.

12. A vision comparison inspection system in accordance with claim 10 wherein said administrative control module further comprises:

administrative mode fiducial display means responsive to administrator input for displaying in said administrative mode primary window zoomed-in portions of said Golden Board image to assist in defining a pair of Golden Board fiducials at selected Golden Board landmarks within each mask-bounded portion of said Golden Board image;

administrative mode target pointer means for generating a movable target image in said administrative mode primary window that assists in precisely defining the locations of said Golden Board fiducials; and administrative mode fiducial definition means responsive to administrator input for defining said Golden Board fiducials at locations indicated by said target image in said administrative mode primary window, and for generating Golden Board fiducial mark images at said fiducial locations.

13. A vision comparison system in accordance with claim 1 wherein said user control module comprises a graphical user interface including a user mode primary window and a user mode overview window, said user mode overview window being adapted for displaying all or a portion of said Test Board image (or said Golden Board image) along with a superimposed user mode viewing rectangle, said user mode primary window being adapted for displaying the portion of said Test Board image (or said Golden Board image) located within said user mode viewing rectangle.

14. A vision comparison inspection system in accordance with claim 9 wherein said user control module further includes image clipping means for applying said mask to said Test Board and Golden Board images to clip said images such that only Test Board and Golden Board image information within said mask is shown when said Test Board and Golden Board images are alternatingly displayed.

15. A vision comparison inspection system in accordance with claim 10 wherein said user control module further includes image clipping means for applying said plural masks to said Test Board and Golden Board images to clip said images such that only Test Board and Golden Board image information within said plural masks is shown when said Test Board and Golden Board images are alternatingly displayed.

16. A vision comparison inspection system in accordance with claim 14 wherein said user control module further includes user-assisted alignment mode means comprising:

user mode alignment display means responsive to user input for displaying in said user mode primary window zoomed-in portions of said Test Board image to assist in placing a pair of Test Board fiducials in the portion of said Test Board image bounded by said mask, at the same landmarks where said pair of Golden Board fiducials were defined;

user mode target box means for generating target boxes in said user mode primary window identifying likely locations of said landmarks where said Golden Board fiducials were defined;

user mode target pointer means for generating a movable target image in said target box that assists in precisely determining the landmark locations for placing said Test Board fiducials;

user mode fiducial placement means responsive to user input for placing said Test Board fiducials at locations indicated by said target image in said target box; and user mode image alignment means for aligning the mask-bounded portion of said Test Board image with the corresponding mask-bounded portion of said Golden Board image using said Golden Board fiducials and said Test Board fiducials.

17. A vision comparison inspection system in accordance with claim 15 wherein said user control module further includes user-assisted alignment mode means comprising:

user mode alignment display means responsive to user input for displaying in said user mode primary window zoomed-in portions of said Test Board image to assist in placing a pair of Test Board fiducials in each of the areas of said Test Board image bounded by said masks, at the same landmarks where said pairs of Golden Board fiducials were defined;

user mode target box means for generating target boxes in said user mode primary window identifying likely locations of said landmarks where said Golden Board fiducials were defined;

user mode target pointer means for generating a movable target image in said target box that assists in precisely determining the landmark locations for placing said Test Board fiducials;

user mode fiducial placement means responsive to user input for placing said Test Board fiducials at locations indicated by said target image in said target box; and user mode image alignment means for aligning the mask-bounded portions of said Test Board image with the corresponding mask-bounded portions of said Golden Board image using said Golden Board fiducials and said Test Board fiducials.

18. A vision comparison inspection system in accordance with claim 14 further including user mode standard sequence means for displaying, according to a standard sequence, predetermined subportions of the mask-bounded portion of said Test Board image in said user mode primary window for vision inspection relative to corresponding subportions of the mask-bounded portion of said Golden Board image.

19. A vision comparison inspect ion system in accordance with claim 15 further including user mode standard sequence means for displaying, according to a standard sequence, predetermined subportions of each mask-bounded portion of said Test Board image in said user mode primary window for vision inspection relative to the corresponding subportions of the plural mask-bounded portions of said Golden Board image, said standard sequence means displaying all of the subportions of a single mask-bounded portion of said Test Board image before displaying subportions of a next mask-bounded portion of said Test Board image.

20. A vision comparison inspection system in accordance with claim 18 wherein said user control module further includes next view means responsive to user input for causing said sequencing means to advance from a current Test Board image subportion view to a next Test Board image subportion view.

21. A vision comparison inspection system in accordance with claim 20 wherein said user control module further includes image view manipulation means responsive to user input for allowing a user to manipulate the view of said Test Board image in said user mode primary window by zooming, panning and scrolling.

22. A vision comparison inspection system in accordance with claim 21 wherein said next view means is responsive to said image view manipulation means being invoked during said standard sequence for returning to the current Test Board image subportion view in its pre-manipulation condition rather than advancing to the next Test Board image subportion view.

23. A vision comparison inspection system in accordance with claim 13 wherein said user control module animation means alternatingly displays a portion of said Golden Board image and a corresponding portion of said Test Board image in said primary window, along with corresponding overview images in said overview window.

24. A vision comparison inspection system in accordance with claim 23 wherein said animation means includes automated animation select means responsive to user input for invoking automated animation and manual animation select means responsive to user input for invoking manual animation wherein user input is required to display each alternate image.

25. A vision comparison inspection system in accordance with claim 13 wherein said user control module further comprises:
 a defect list box in said user mode graphical user interface;
 defect marking means responsive to user input for placing a defect mark in said user mode primary window indicating a defect in said Test Board;
 defect identification means responsive to user input for identifying the nature of said defect;
 defect list means for generating a defect entry in said defect list box corresponding to said defect; and
 defect storage means for storing information relative to said defect in one or more records of a defect log file.

26. A vision inspection system in accordance with claim 25 wherein said defect marking means and said defect identification means are responsive to the same user input, said defect identification means being responsive to said input by generating a pop-up menu displaying a list of possible defects and said marking means being responsive to said user input and a user selecting one of said possible defects for placing said defect mark.

27. A vision comparison inspection system in accordance with claim 26 wherein said user control module further includes defect source means responsive to a user selecting one of said possible defects for spawning a second pop-up menu displaying a list of possible defect sources.

28. A vision comparison inspection system in accordance with claim 25 wherein said user control module further includes defect count means for displaying the number of defects listed in said defect list box.

29. A vision comparison inspection system in accordance with claim 28 wherein user control module further includes defect resolution means activatable following said standard sequence for specifying a resolution action taken with respect to said defect and listing said resolution action in said defect list box in association with said defect.

30. A vision comparison inspection system in accordance with claim 29 wherein said user control module further includes Test Board release disable means for disabling the release of said Test Board from said vision comparison inspection system until all defects listed in said defect list box have been resolved.

31. A vision comparison inspection system in accordance with claim 30 wherein the defect information stored by said defect storage means includes within each record of said defect log file a plurality of fields containing information about defect type, defect location on said Test Board, and defect resolution.

32. A vision comparison inspection system in accordance with claim 31 wherein the defect information stored by said defect storage means further includes within each record of said defect log file a field containing defect source information.

33. A vision comparison inspection system in accordance with claim 32 wherein the defect information stored by said defect storage means further includes for each record a plurality of fields containing a Test Board identifier, a path and filename of a corresponding one of said Golden Board files, an operator identifier, and a date and time stamp.

34. A vision comparison inspection system in accordance with claim 13 wherein said user control module further includes Test Board-to-Golden Board promotion means responsive to a Test Board having no errors for allowing a user to promote a Test Board to a Golden Board.

35. A vision comparison inspection system in accordance with claim 16 wherein said user control module further includes Test Board-to-Golden Board promotion means responsive to a Test Board having no errors for allowing a user to promote a Test Board to a Golden Board, said promotion means including administrative module invocation means responsive to a user selecting to promote a Test Board to a Golden Board, whereby said user may then elect to use said Test Board image or capture a new image of said Test Board, and may further elect to use the masks and fiducial marks defined for the prior Golden Board, or define new masks and fiducials for the newly promoted Test Board.

36. A vision comparison inspection system in accordance with claim 16 wherein said user control module further includes fiducial mode invocation means responsive to user input for activating said user-assisted alignment mode means.

37. A vision comparison inspection system in accordance with claim 36 wherein said user control module further includes Re-Align selection means responsive to said fiducial mode invocation means being activated for aligning a current Test Board that has not been previously aligned, for realigning a current Test Board that was previously aligned, and for undoing an alignment that was previously performed on a current Test Board, respectively.

38. A vision comparison inspection system in accordance with claim 13 wherein said user control module further includes board release means for releasing said printed circuit assemblies from an inspection location, respectively.

39. A vision comparison inspection system in accordance with claim 13 wherein said user control module further includes animation rate control means for allowing a user to change the rate at which said Test Board and Golden Board images are alternatingly displayed in said user mode primary window.

40. A vision comparison inspection method for use in association with a printed circuit assembly production line, comprising the steps of:
 positioning one or more printed circuit assemblies under test (Test Board(s)) within the field of view of an electronic image capture device that is fixedly positioned to capture an image of the entirety of said Test Board(s) at sufficient resolution to allow vision inspection of said Test Board(s);

illuminating said Test Board(s) with a lighting system;

controlling said imaging device to acquire an image of said Test Board(s) (Test Board image) and to transfer said image to an image control system having an information storage device, an electronic display device, an input device, and a programmed image processing computer;

controlling said imaging control system to process said Test Board image for inspection and to perform animation by alternatingly displaying on said display device said Test Board image and the stored image of one or more corresponding known good printed circuit assemblies (Golden Board(s)) (Golden Board image), whereby defects in said Test Board(s) can be visually revealed, said Golden Board image being stored in a Golden Board file;

said method further including the steps of (1) defining one or more masks in said Golden Board image in correspondence with the number of Golden Boards displayed in said Golden Board image, (2) storing said mask(s) in a parameter file associated with said Golden Board file, and (3) automatically applying said mask(s) to said Test Board and Golden Board images to clip said Test Board and Golden Board images to remove unnecessary information therefrom and alternatingly display only portions of said Test Board and Golden Board images that are bounded by said mask(s); and said method additionally including the steps of (1) defining a pair of Golden Board fiducials within each mask defined in said Golden Board image so as to correspond to identifiable landmarks in said Golden Board, (2) storing said Golden Board fiducials in said parameter file, (3) placing a pair of Test Board fiducials within each portion of said Test Board image bounded by said mask(s) at the same landmarks used for defining said Golden Board Fiducials and (4) aligning each mask-bounded portion of said Test Board image with a corresponding mask-bounded portion of said Golden Board image using said Golden Board fiducials and said Test Board fiducials.

41. A vision comparison inspection method in accordance with claim 40 further including the steps of generating a log of defects found in said Test Board and storing said defect log in one or more records of a defect log file.

42. A vision comparison inspection method in accordance with claim 41 wherein said defect log contains a record for each defect listed therein that includes fields containing information about defect type, defect location on said Test Board, and defect resolution.

43. A vision comparison inspection method in accordance with claim 42 wherein said defect log records further contain a field containing defect source information.

44. A vision comparison inspection system for use in association with a printed circuit assembly production line, said inspection system, comprising:

an electronic image capture device fixedly positioned to capture an image of the entirety of one or more printed circuit assemblies under test (Test Board(s));

a lighting system for illuminating said Test Board(s);

an imaging control system receiving the output of said image capture device and including a programmed image processing computer, an electronic display device and an input device;

an administrative control module in said imaging control system for creating files containing images and other information (Golden Board images) corresponding to one or more known good circuit assemblies (Golden Board(s)), said administrative control module comprising an administrative mode graphical user interface (Administrative Mode GUI) including an administrative mode primary window and an administrative mode overview window, said administrative mode overview window displaying one of said Golden Board images and an administrative mode viewing rectangle superimposed over said Golden Board image, said administrative mode primary window displaying the portion of said Golden Board image located within said administrative mode viewing rectangle; and a user control module in said imaging control system for processing said Test Board image based on information in one of said Golden Board files and performing animation by alternatingly displaying said Golden Board image and said Test Board image on said display device, whereby defects in said Test Board can be visually identified, said user control module comprising a user mode graphical user interface (User Mode GUI) including a user mode primary window and a user mode overview window, said user mode overview window displaying said Test Board image (or said Golden Board image) and a user mode viewing rectangle superimposed over said Test Board image, said user mode primary window displaying the portion of said Test Board image (or said Golden Board image) located within said viewing rectangle;

administrative mode mask display mask means responsive to administrator input to said Administrative Mode GUI for displaying the entirety of said Golden Board image in said administrative mode primary window;

administrative mode mask generation means responsive to administrator input to said Administrative Mode GUI for generating an adjustably sizeable mask outline in said administrative mode primary window;

administrative mode mask definition means responsive to administrator input to said Administrative Mode GUI for defining one or more masks corresponding to said mask outline that delimits said Golden Board image and bounds said Golden Board(s) displayed therein;

user mode image clipping means for automatically applying said mask(s) to said Test Board and Golden Board images to eliminate unnecessary information and display only portions of said Test Board and Golden Board images bounded by said mask(s);

administrative mode fiducial means responsive to input from an administrator to said Administrative Mode GUI for defining a pair of Golden Board fiducials within each mask defined in said Golden Board image in association with identifiable landmarks on said Golden Board(s), and for generating Golden Board fiducial marks to identify the locations of said Golden Board fiducials;

use mode image alignment means responsive to input from a user to said User Mode GUI for placing Test Board fiducials in each mask-bounded portion of said Test Board image and for aligning the mask bounded portion(s) of said Test Board image with the mask-bounded portion(s) of said Golden Board image using said Golden Board fiducials and said Test Board fiducials; and defect log means responsive to input from a user to said User Mode GUI for generating a log of defects found in said Test Board and storing said defect log in one or more records of a defect log file.

* * * * *